United States Patent
Schulze et al.

(10) Patent No.: US 11,332,692 B2
(45) Date of Patent: May 17, 2022

(54) COMPOSITION FOR ODOUR IMPROVEMENT

(71) Applicant: Symrise AG, Holzminden (DE)

(72) Inventors: Nicole Schulze, Freden (DE); Claudia Schmidt, Stahle (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 16/609,992

(22) PCT Filed: May 5, 2017

(86) PCT No.: PCT/EP2017/060745
§ 371 (c)(1),
(2) Date: Oct. 31, 2019

(87) PCT Pub. No.: WO2018/202311
PCT Pub. Date: Nov. 8, 2018

(65) Prior Publication Data
US 2020/0056118 A1  Feb. 20, 2020

(51) Int. Cl.
*C11B 9/00* (2006.01)
*A61K 8/34* (2006.01)
(Continued)

(52) U.S. Cl.
CPC ............. *C11B 9/0015* (2013.01); *A61K 8/33* (2013.01); *A61K 8/34* (2013.01); *A61K 8/361* (2013.01);
(Continued)

(58) Field of Classification Search
CPC .................................................. A61K 8/361
See application file for complete search history.

(56) References Cited

U.S. PATENT DOCUMENTS

2006/0052276 A1* 3/2006 Perring .................... A61K 8/37
512/1

FOREIGN PATENT DOCUMENTS

WO   WO-2015062997 A1 *  5/2015  ............. A61Q 19/00
WO   2016/049389 A1   3/2016

OTHER PUBLICATIONS

Espacenet search_Oct. 21, 2020_geraniol odor masking (Year: 2020).*

(Continued)

*Primary Examiner* — Michael P Cohen
(74) *Attorney, Agent, or Firm* — Dilworth & Barrese, LLP

(57) ABSTRACT

The invention relates to a preparation containing: (i) a composition containing (a) one, two or a plurality of compounds selected from the group consisting of (a1) alcohol monoterpenes of formula (I) in which R1 is H or methyl, R2 is H or $C_2$-alkenyl, und R3 is a linear or branched, saturated or unsaturated hydrocarbon radical with 4 to 10 carbon atoms, and the enantiomers, diastereomers, racemates, solvates and physiologically compatible salts thereof, and/or (a2) bicyclic epoxy-monoterpenes, (b) at least two lactones of formula (II) in which R4 is H or methyl, R5 is a linear or branched, saturated or unsaturated hydrocarbon radical with 2 to 10 hydrocarbon atoms and n is the number 1 or 2, and the enantiomers, diastereomers and racemates thereof, (c) one, two or a plurality of solvents selected from the group consisting of ethanol, water, dipropylene glycol (DPG), diethyl phtalate (DEP), propylene glycol (PG), isopropyl myristate (IPM), isopropyl palmitate (IPP), triethyl citrate (TEC), triacetin (TRI), 1,2-Propanediol, 1,3-Propanediol, Propanethiol, Pentanediol, Hexanediol, Octanediol, Decanediol (SymClariol®), Dodecanol, 4-hydroxy-acetophenone (SymSave® H), glycerine, butylene glycol, pentylene glycol, hexylene glycol, decylene glycol, propylene carbonate, butylene carbonate, glycerine carbonate, 2-5 benzyl heptanol, lauryl alcohol, trimethyl-hydroxypentyl-isobutyrate, glyceryl-caprylate, ethylhexyl glycerine, benzyl benzoate (BB), and optionally (d) other flavouring agents or aromatic substances selected from the group consisting of 3-phenylbutanal (Trifernal), acetyl methyl carbinol, anethole, anisyl acetate, dihydroeugenol, linalyl formate, 2-methyldecanal, 2-benzyl-2-methylbut-3-ene nitrile (Ci-Trowanil® B), 3-hexenyl acetate, styrallyl acetate, belanis, citronellal, cinnamyl acetate, rhubafuran, beta-ions, anther, prenyl acetate, 2-phenyl propanal, 4-(4-hydroxyphenyl)butan-2-one (Frambinon®), ethyl phenoxyacetate, isoralderine, gamma-terpinene, limonene, neocyclocitral, methyl lavender ketone, styrallyl propionate, phenyl ethyl propionate, limonenal, 4-isopentylcyclohexanol (Symrose®), 4-methyl-2-phenyl-3,6-dihydro-2H-pyran/4-methylene-2-phenyl-tetrahydropyrane (Rosyrane super), hydrocitronitril, phenoxanol, isoamyl phenylacetate, damascone, silvial, nectaryl, ambroxide, acetyl pyrazine, trimethyl pyrazine, isoamyl acetate, para-cresyl methyl ether, filbertone, cyclohexyl acetate, heliotropin, acetophenone, anisaldehyde, paramethyl acetophenone, veratraldehyde, methyl anisate and vertoprenal; (ii) aldehydes of formula (III) in which R6 is a saturated or non-saturated, linear hydrocarbon radical; and/or (iii) free fatty acids of formula (IV), in which R7 is a linear or branched, saturated hydrocarbon radical.

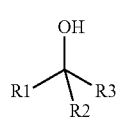

(I)

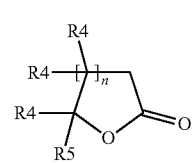

(II)

(Continued)

-continued

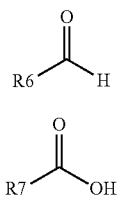

(III)

(IV)

4 Claims, No Drawings

(51) Int. Cl.
*A61K 8/49* (2006.01)
*A61K 8/33* (2006.01)
*A61K 8/36* (2006.01)
*A61Q 1/14* (2006.01)
*A61Q 5/02* (2006.01)
*A61Q 5/12* (2006.01)
*A61Q 19/00* (2006.01)
*A61Q 19/10* (2006.01)
*A61Q 13/00* (2006.01)
*C11D 3/00* (2006.01)
*C11D 3/50* (2006.01)

(52) U.S. Cl.
CPC .............. *A61K 8/4973* (2013.01); *A61Q 1/14* (2013.01); *A61Q 5/02* (2013.01); *A61Q 5/12* (2013.01); *A61Q 13/00* (2013.01); *A61Q 19/001* (2013.01); *A61Q 19/10* (2013.01); *C11B 9/0019* (2013.01); *C11B 9/0076* (2013.01); *C11D 3/001* (2013.01); *C11D 3/50* (2013.01)

(56) References Cited

OTHER PUBLICATIONS

Google Patent Search_Oct. 21, 2020_geraniol mask odor of oleochemicals (Year: 2020).*
Google Scholar Search_Oct. 22, 2020_masking oleochemical malodor (Year: 2020).*

* cited by examiner

COMPOSITION FOR ODOUR IMPROVEMENT

FIELD OF THE INVENTION

The invention is in the field of oleochemical products and relates to substance mixtures which reduces or prevents the sensory perception of substances which are formed by oleochemical preparations and cause undesired off-notes and to a method for the production thereof and to the use thereof.

PRIOR ART

Oleochemical products and preparations from the cosmetics, household, oral care product and fine fragrance sectors contain fats, fatty acids, fatty acid esters, fatty acid salts or fat- or fatty acid-based ingredients. What is common to all these substances is that they have a typical fatty odor, which additionally develops further unpleasant notes in the event of relatively long storage. Causes thereof are not only short-chain free fatty acids which are released by saponification of triglycerides, but also especially aldehydes and other substances which arise by oxidation.

These undesired off-notes have an adverse effect on the odor or aroma of the product or preparation and the quality thereof. Common perfuming agents or fragrances/aromas that are used can mask said off-notes only to a limited extent and must be used in increased concentration if necessary, and this in turn results in increased costs.

One way of solving this problem is to subject batches objectionable in terms of odor to a posttreatment, to so-called deodorization. This involves treating the raw materials with hot water vapor, with the odor carrier being distilled off to a great extent. However, the method is associated with a high input of energy. This measure is naturally counterproductive from an economical point of view, especially when what is concerned is processing fats and oils which are as inexpensive as possible and which by nature have the highest proportion of the stated undesired odor carriers.

In some cases, it is also possible to enclose the unpleasant odor by addition of an encapsulator, as described for example in WO 2009 131748 A1. However, this measure is also hardly realizable from an economical perspective. In the case of this solution, there is the possibility that odorants or aroma substances of the added aromatization or perfuming agent might likewise be bound by the encapsulator and may as a result have an adverse effect on the desired fragrance or taste.

To date, the most common alternative has been to add fragrances to the olfactorily objectionable raw materials—or to the end products manufactured therewith—which fragrances cover (mask) the unpleasant odor or aroma or combine therewith in such a way that a new odor or aroma which is less unpleasant is formed. This method, too, is complex and expensive, since considerable amounts of such masking substances have always been necessary to date.

Document EP 2 865 739 A1 discloses the use of mixtures containing lactones of formula (Ia) or (Ib)

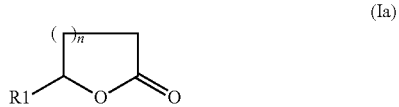

(Ia)

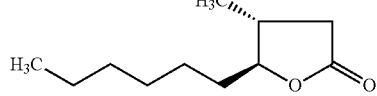

(Ib)

where R1 is a linear or branched, saturated or unsaturated, optionally hydroxy-substituted hydrocarbon radical having 2 to 22 carbon atoms and 0 or 1 to 3 double bonds and n is the numbers 1 or 2, for the masking of odor off-notes in oleochemical preparations.

Document WO 03/070871 A1 relates to a composition for the counteracting and/or masking of malodor which develops during the soaking and/or handwashing of laundry. The disclosed compositions comprise one or more malodor-suppressing substances selected from the group consisting of: compounds of formula (I), aldehyde C-11 (undecanal), aldehyde C-11 inter, aldehyde C-12 lauric acid, ethyl rosate, galbanum oil, hivertal, methyl cresol para, methylacetophenone, patchouli oil, undecavertol, aldehyde C-11 lenic, allyl cyclohexyl propionate, ambrettolide, amyl salicylate, damascone delta, dihydromyrcenol, ethylvanillin, florazone, irisnitrile, methyl ionone gamma, nonalactone gamma, pandanol, rose oxide L and tridecene-2-nitrile.

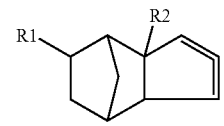

Compounds of Formula (I) According to WO 03/070871 A1

Document US 2006/0207037 A1 discloses a perfume or odorant mixture which is optimized for the covering of malodors caused by nitrogenous substances, such as ammonia and substituted amines, but which can also be used for other types of malodors such as sweat, body odor, bathroom odors, kitchen odors, etc. Furthermore, fragrance mixtures are disclosed which exhibit the combinations of gamma-undecalactone, gamma-decalactone and diethyl phthalate (DEP) and also the combination of gamma-undecalactone, geraniol, linalool and diethyl phthalate (DEP). The main use of these odorant mixtures are hair colorants, though they can also be used for products ranging from household cleaners to cosmetics, encompassing antiperspirants, deodorants, self-tanners, shampoos, conditioners, hand lotion, body lotion and perming agents.

Document WO 2004/009750 A1 describes fragrance components, mixtures thereof and perfume compositions for the reduction or prevention of body odor. The identified fragrance components prevent the production of odorous steroids, which are produced by microorganisms present on the skin surface. The compositions are described as antimalodor active substance and as deodorant active substance for cosmetics or perfume, antiperspirants and deodorants. The combination of gamma-octalactone, gamma-nonalactone, geraniol, dihydrolinalool and tetrahydrogeraniol is disclosed.

Document WO 96/04940 relates to an aqueous composition for the reduction of the perception of an unpleasant or bad odor, comprising: a) about 0.01% to about 1% of perfume, based on the weight of the composition; b) optionally, but preferably, about 0.1% to about 5% of a water-soluble cyclodextrin, based on the weight of the composition; c) optionally, but preferably, about 0.1% to about 10% of a water-soluble metal salt, based on the weight of the composition; d) optionally, but preferably, about 0% to about 3% of a solubilizing aid, based on the weight of the composition; and e) an aqueous carrier. Gamma-decalactone and gamma-dodecalactone are among the various fragrances which component a) can contain. The composition are preferably sprayed onto textiles, especially clothes, without washing or dry-cleaning them.

Despite the abovementioned alternatives known from the prior art, there continues to be a strong need in the field of oleochemical products for novel substance mixtures which overcome the abovementioned disadvantages and which allow the production of qualitatively high-value products and preparations without undesired odor or aroma off-notes.

Furthermore, said undesired off-notes also have an effect on the utilization of the products or preparations, since the common perfuming agents or aromatization agents fail during washing, spraying or creaming and the undesired off-notes stand out particularly strongly.

It is therefore an object of the present invention to provide novel, highly active substance mixtures which, even in very low concentrations, are capable of counteracting, reducing or masking the unpleasant odor or aroma off-notes which occur in oleochemical raw materials and in the end products produced therewith, preferably off-notes which are perceived by the consumers as pungent, irritating, oxidized, acrid, rancid, fatty, animalistic, goat, fermented, musty, herbaceous and vomit.

It is therefore a second object of the present invention to provide novel, highly active substance mixtures which are capable of counteracting, reducing or masking the abovementioned undesired off-notes, both during utilization and after rinse-off of the oleochemical preparations or end products, especially from the skin surface, which comprise said highly active substance mixtures.

DESCRIPTION OF THE INVENTION

The present invention provides in a first aspect preparations containing (i) a substance mixture containing
   (a) one, two or more compounds selected from the group consisting of
      (a1) alcohol monoterpenes of formula (I)

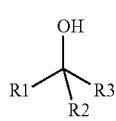

where
      R1 is H or methyl, R2 is H or $C_2$-alkenyl, and R3 is a linear or branched, saturated or unsaturated hydrocarbon radical having 4 to 10 carbon atoms, and also the enantiomers, diastereomers, racemates, solvates and physiologically compatible salts thereof, and/or
   (a2) bicyclic epoxy monoterpenes,
(b) at least two lactones of formula (II)

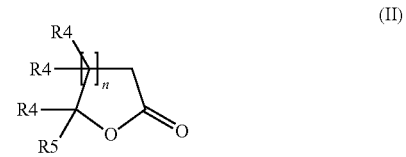

where
      R4 is H or methyl, R5 is a linear or branched, saturated or unsaturated hydrocarbon radical having 2 to 10 carbon atoms and n is the numbers 1 or 2, and also the enantiomers, diastereomers and racemates thereof, and
(c) one, two or more solvents selected from the group consisting of ethanol, water, dipropylene glycol (DPG), diethyl phthalate (DEP), propylene glycol (PG), isopropyl myristate (IPM), isopropyl palmitate (IPP), triethyl citrate (TEC), triacetin (TRI), 1,2-propanediol, 1,3-propanediol, propanethiol, pentanediol, hexanediol, octanediol, decanediol (SymClariol®), dodecanol, 4-hydroxyacetophenone (SymSave® H), glycerol, butylene glycol, pentylene glycol, hexylene glycol, decylene glycol, propylene carbonate, butylene carbonate, glycerol carbonate, 2-benzylheptanol, lauryl alcohol, trimethyl hydroxypentyl isobutyrate, glyceryl caprylate, ethylhexylglycerin, benzyl benzoate (BB), and optionally
(d) further aroma substances or fragrances selected from the group consisting of 3-phenylbutanal (trifernal), acetylmethylcarbinol, anethole, anisyl acetate, dihydroeugenol, linalyl formate, 2-methyldecanal, 2-benzyl-2-methylbut-3-enenitrile (Citrowanil® B), 3-hexenyl acetate, styralyl acetate, belanis, citronellal, cinnamyl acetate, rhubafuran, beta-ionone, anther, prenyl acetate, 2-phenylpropanal, 4-(4-hydroxyphenyl)butan-2-one (Frambinon®), ethyl phenoxyacetate, isoraldeine, gamma-terpinene, limonene, neocyclocitral, methyl lavender ketone, styralyl propionate, phenethyl propionate, limonenal, 4-isopentylcyclohexanol (Symrose®), 4-methyl-2-phenyl-3,6-dihydro-2H-pyran/4-methylene-2-phenyltetrahydropyran (Rosyrane super), hydrocitronitrile, phenoxanol, isoamyl phenylacetate, damascone, silvial, nectaryl, ambroxide, acetyl pyrazine, trimethyl pyrazine, isoamyl acetate, para-cresyl methyl ether, filbertone, cyclohexyl acetate, heliotropin, acetophenone, anisaldehyde, para-methyl acetophenone, veratraldehyde, methyl anisate and vertoprenal,
and
(ii) aldehydes of formula (III)

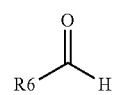

where R6 is a saturated or unsaturated, linear hydrocarbon radical, and/or
(iii) free fatty acids of formula (IV)

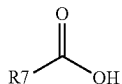

where R7 is a linear or branched, saturated hydrocarbon radical.

In a preferred embodiment, the preparation according to the invention is an oleochemical preparation.

In a preferred embodiment, the preparation according to the invention contains at least two, three or four substances of group (a).

In a further preferred embodiment, component (a1) is selected from the group consisting of linalool, geraniol, freesiol and nerolidol and also the enantiomers, diastereomers, racemates, solvates and physiologically compatible salts thereof.

In a further preferred embodiment, the bicyclic epoxy monoterpenes (component (a2)) are epoxy-p-menthane derivatives, and particular preference is given to the compounds 1,4-cineole and 1,8-cineole.

In a preferred embodiment, the preparation according to the invention contains at least two lactones—optionally three or four—selected from the group consisting of the lactones of formula (II) and also the enantiomers, diastereomers and racemates thereof, where R4 is H, R5 is linear and saturated hydrocarbon radicals having 2 to 10 carbon atoms and n is the numbers 1 or 2, particularly preferably where R4=H and R5=linear and saturated hydrocarbon radicals having 2 to 8 carbon atoms and n=1 or 2.

In a further preferred embodiment, the preparation according to the invention contains at least two lactones—optionally three or four—selected from the group consisting of gamma-dodecalactone, gamma-decalactone, gamma-undecalactone, delta-decalactone, delta-dodecalactone, 4-methyl-gamma-nonalactone, 3-methyl-gamma-decalactone, gamma-nonalactone, delta-nonalactone, gamma-octalactone, delta-octalactone, gamma-heptalactone, delta-heptalactone, gamma-hexalactone and delta-hexalactone, preferably gamma-dodecalactone, gamma-decalactone, delta-decalactone and delta-dodecalactone.

In a preferred embodiment, the aldehydes of formula (III) are selected from the group consisting of hexanal, heptanal, octanal, nonanal, decanal, hexenal, heptenal, octenal, nonenal, decenal, undecenal, dodecenal, hexadienal, heptadienal, octadienal, nonadienal, decadienal, undecadienal, dodecadienal, octatrienal, nonatrienal, decatrienal, undecatrienal, dodecatrienal, especially preferably hexanal, octanal, nonanal, hexenal, heptenal, octenal, heptadienal, octadienal, decadienal and decatrienal.

In a further preferred embodiment, the free fatty acids of formula (IV) are selected from the group consisting of butanoic acid, pentanoic acid, isovaleric acid, hexanoic acid, heptanoic acid, octanoic acid, nonanoic acid, decanoic acid, undecanoic acid and dodecanoic acid, especially preferably hexanoic acid, octanoic acid and decanoic acid.

In another preferred embodiment, the aldehydes of formula (III) are selected from the group consisting of hexanal, heptanal, octanal, nonanal, decanal, hexenal, heptenal, octenal, nonenal, decenal, undecenal, dodecenal, hexadienal, heptadienal, octadienal, nonadienal, decadienal, undecadienal, dodecadienal, octatrienal, nonatrienal, decatrienal, undecatrienal, dodecatrienal, especially preferably hexanal, octanal, nonanal, hexenal, heptenal, octenal, heptadienal, octadienal, decadienal and decatrienal,
and
the free fatty acids of formula (IV) are selected from the group consisting of butanoic acid, pentanoic acid, isovaleric acid, hexanoic acid, heptanoic acid, octanoic acid, nonanoic acid, decanoic acid, undecanoic acid and dodecanoic acid, especially preferably hexanoic acid, octanoic acid and decanoic acid.

In a preferred embodiment, component (c) of the preparation according to the invention is one, two or more solvents selected from the group consisting of ethanol, water, dipropylene glycol (DPG), diethyl phthalate (DEP), propylene glycol (PG), isopropyl myristate (IPM), isopropyl palmitate (IPP), triethyl citrate (TEC), triacetin (TRI), 1,2-propanediol, 1,3-propanediol, propanethiol, pentanediol, hexanediol, octanediol, decanediol (SymClariol®), dodecanol, 4-hydroxyacetophenone (SymSave® H) and benzyl benzoate (BB).

In a further preferred embodiment, the preparation according to the invention contains one or more aroma substances or fragrances of group (d), these being selected from the group of 3-phenylbutanal (trifernal), acetylmethylcarbinol, 2-methyldecanal, 2-benzyl-2-methylbut-3-enenitrile (Citrowanil® B), 3-hexenyl acetate, styralyl acetate, rhubafuran, anther, prenyl acetate, styralyl propionate, isoamyl phenylacetate, beta-damascone, isoamyl acetate, citronellol and cyclohexyl acetate.

In the context of the present invention, the preparation according to the invention can be combined with additional fragrances or aroma substances.

The present invention therefore further provides a fragrance or aroma composition containing the preparation according to the invention in combination with additional fragrances or aroma substances of group (e) that can be incorporated in oleochemical preparations or end products.

Fragrances or aroma substances of group (e) in the context of the invention are substances which are defined by, for example, European or American jurisprudence, for example Regulation (EC) No 2232/96 of the European Parliament and of the Council and the positive list as per Commission Implementing Regulation (EU) No 872/2012, and the substances which are listed in "*Riechstoffe*" [Odorants] by Steffen Arctander, in "*Perfume and Flavor Chemicals*" by Eigenverlag, Montclair, N.J. 1969 and in "*Common Fragrance and Flavor Materials*" by H. Surburg, J. Panten, 5th edition, Wiley-VCH, Weinheim 2006.

Examples of fragrances and aroma substances of group (e) in the context of the invention are
extracts from natural raw materials such as essential oils, concretes, absolutes, resins, resinoids, balsams, tinctures such as, for example, ambra tincture; amyris oil; angelica seed oil; angelica root oil; anis oil; valerian oil; basil oil; tree moss absolute; bay oil; mugwort oil; benzoin resin; bergamot oil; beeswax absolute; birch tar oil; bitter almond oil; savory oil; bucco leaf oil; cabreuva oil; cade oil; calmus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill oil; dill seed oil; eau de brouts absolute; oakmoss absolute; elemi oil; estragon oil; eucalyptus citriodora oil; eucalyptus oil; fennel oil; pine needle oil; galbanum oil; galbanum resin; geranium oil; grapefruit oil; guaiac wood oil;

gurjun balsam; gurjun balsam oil; helichrysum absolute; helichrysum oil; ginger oil; iris root absolute; iris root oil; jasmine absolute; calamus oil; camellia oil blue; camellia oil roman; carrot seed oil; cascarilla oil; pine needle oil; spearmint oil; cumin oil; labdanum oil; labdanum absolute; labdanum resin; lavandin absolute; lavandin oil; lavender absolute; lavender oil; lemon grass oil; lovage oil; lime oil distilled; lime oil pressed; linalool oil; litsea cubeba oil; laurel leaf oil; macis oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; oregano oil; palmarosa oil; patchouli oil; perilla oil; Peruvian balsam oil; parsley leaf oil; parsley seed oil; petitgrain oil; peppermint oil; pepper oil; allspice oil; pine oil; poley oil; rose absolute; rosewood oil; rose oil; rosemary oil; sage oil dalmatian; sage oil Spanish; sandalwood oil; celery seed oil; spike lavender oil; star anis oil; styrax oil; tagetes oil; fir needle oil; tea tree oil; turpentine oil; thyme oil; tolu balsam; tonka absolute; tuberose absolute; vanilla extract; violet leaf absolute; verbena oil; vetiver oil; juniper berry oil; wine yeast oil; vermouth oil; wintergreen oil; ylang oil; ysop oil; civet absolute; cinnamon leaf oil; cinnamon bark oil, and fractions thereof or ingredients isolated therefrom esters such as, for example, ethyl butyrate, allyl caproate, benzyl acetate, methyl salicylate, neryl acetate, geranyl acetate, allyl caproate, anisyl formate, butyl butyrate, butyl caproate, butylidene phthalide, benzyl benzoate, citronellyl acetate, dimethyl anthranilate, dimethyl anthranilate, ethoxyethyl acetate, ethyl butyrate, ethyl caprate, ethyl caproate, ethyl crotonate, ethyl isobutyrate, ethyl isovalerate, ethyl lactate, ethyl methyl butyrate, ethyl propionate, ethyl heptylate, methyl dihydrojasmonate (e.g., Hedion®), cis-2-hexenyl acetate, cis-3-hexenyl caproate, trans-2-hexenyl caproate, cis-3-hexenyl formate, cis-2-hexyl acetate, cis-3-hexyl acetate, trans-2-hexyl acetate, cis-3-hexyl formate, isoamyl isovalerate, isobutyl butyrate, linalyl acetate, methyl anthranilate, 2-methylbutyl acetate, methyl caproate, methyl cinnamate, methyl jasmonate, 2-methylmethyl butyrate, methyl thiobutyrate, 3-methylthiohexyl acetate, neryl acetate, 1-octyl acetate, 3-octyl acetate, phenethyl acetate, phenethyl isovalerate, propyl butyrate, ethylvanillin isobutyrate, acetic acid isoamyl ester, butyric acid ethyl ester, butyric acid n-butyl ester, butyric acid isoamyl ester, 3-methylbutyric acid ethyl ester, n-hexanoic acid ethyl ester, n-hexanoic acid allyl ester, n-hexanoic acid n-butyl ester, n-octanoic acid ethyl ester, ethyl 3-methyl-3-phenylglycidate, ethyl 2-trans-4-cis-decadienoate, methyl salicylate, methyl sorbate;

alcohols such as, for example, octenol, cis-3-hexanol, benzyl alcohol, phenethyl alcohol, eugenol, cis-3-hexenol, isoamyl alcohol, methylbutanol, 3,1-methylthiohexanol, 2,4-nonadienol, 2,6-nonadienol, 2,4-nonadienol, 2-octanol, 3-octanol, 1,3-octenol, phenethyl alcohol, phenethyl alcohol, cinnamyl alcohol;

aldehydes such as, for example, acetaldehyde, isobutyraldehyde, nonadienal, 3-phenylacetaldehyde, benzaldehyde, grapefruit aldehyde, isobutyraldehyde, 5-methyl furfural, paraldehyde, piperonal, propionaldehyde, vanillin, ethylvanillin, divanillin, phenylacetaldehyde, methional, cinnamaldehyde;

ketones such as, for example, menthone, alpha-ionone, beta-ionone, 4-(p-hydroxyphenyl)-2-butanone, 2-heptanone, 3-heptanone, 4-heptanone, para-hydroxybenzylacetone, 3,2,2-methylcyclopentenolone, 6,5,2-methylheptenone, nootkatone, pentanedione, 4-(p-hydroxyphenyl)-2-butanone;

ethers such as, for example, 4-hydroxy-5-methylfuranone, 3-hydroxy-4,5-dimethyl-2(5H)-furanone, 2,5-dimethyl-3-hydroxy-2(3H)-furanone, 2(5)-ethyl-4-hydroxy-5(2)-methyl-3(2H)-furanone, p-methoxybenzaldehyde, guaiacol, methoxyvinylphenol, ethyl furaneol, ethyl guaiacol, isoeugenol methyl ether, menthofuran, 2,5-dimethyl-4-hydroxy-3(2H)-furanone, homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone, 1,1-dimethoxy-2,2,5-trimethyl-4-hexane;

acetals such as, for example, acetaldehyde diethyl acetal; heliotropine diethyl acetal;

lactones such as, for example, ethylene brassylate, Globalide®, ambrettolide, massoilactone, tuberolactone, 4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecandioate; ethylene-1,13-tridecandioate; coumarin; 2,3-dihydrocoumarin; octahydrocoumarin;

terpenes such as, for example, citronellol; nerol; lavadulol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates, 3-methyl-2-butenoates thereof;

terpene aldehydes such as, for example, geranial; neral; citronellal; 7-hydroxy-3,7-dimethyloctanal; 7-methoxy-3,7-dimethyloctanal; 2,6,10-trimethyl-9-undecenal; geranyl acetone and the dimethyl and diethyl acetals of geranial, neral and 7-hydroxy-3,7-dimethyloctanal; menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates thereof;

cyclic terpene alcohols such as, for example, menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates thereof;

sulfides and disulfides such as, for example dimethyl sulfide, difurfuryl disulfide, methylthiopropanal;

thiols such as, for example, methylfuranthiol, benzothiazole, isopropylmethylthiazole, sulfurol, 8,3-thiomenthanone, 4,4,2-thiomethylpentanone, 2,4,5-trimethylthiazole, 2-acetylthiazole, 2,4-dimethyl-5-ethylthiazole;

pyrazines and pyrrolines such as, for example, methylpyrazine, acetylpyrazine, 2-propionylpyrroline, 2-acetylpyrroline, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-pentylpyridine cycloaliphatic alcohols such as, for example, alpha,3,3-trimethylcyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

cyclic and cycloaliphatic ethers such as, for example, cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

cyclic and macrocyclic ketones such as, for example, 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 7-cyclohexadecen-1-one; 8-cyclohexadecen-1-one; 9-cycloheptadecen-1-one; cyclopentadecanone; cyclohexadecanone;

cycloaliphatic aldehydes such as, for example, 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

cycloaliphatic ketones such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl 2,4-dimethyl-3-cyclohexen-1-yl ketone;

esters of cyclic alcohols such as, for example, 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or -6-indenyl acetate; 4,7-methano-3a,4,5,6,7,7a-hexahydro-5- or -6-indenyl propionate; 4,7-methano-3a,4,5,6,7,7a-hexahydro-5- or -6-indenyl isobutyrate; 4,7-methanooctahydro-5- or -6-indenyl acetate;

esters of cycloaliphatic carboxylic acids such as, for example, allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

araliphatic alcohols such as, for example, benzyl alcohol; 1-phenethyl alcohol; 2-phenethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl) ethanol;

araliphatic ethers such as, for example, 2-phenethyl methyl ether; 2-phenethyl isoamyl ether; 2-phenylethyl 1-ethoxyethyl ether; phenylacetaldehyde dimethyl acetal; phenylacetaldehyde diethyl acetal; hydratropic aldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes such as, for example, benzaldehyde; phenylacetaldehyde; 3-phenylpropanal; hydratropic aldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

aromatic and araliphatic ketones such as, for example, 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

aromatic and araliphatic carboxylic acids and esters thereof such as, for example, benzoic acid; phenylacetic acid; methyl benzoate; ethyl benzoate; hexyl benzoate; benzyl benzoate; methylphenyl acetate; ethylphenyl acetate; geranylphenyl acetate; phenethyl phenylacetate; methyl cinnmate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenethyl salicylate; methyl 2,4-dihydroxy-3,6-dimethylbenzoate; ethyl 3-phenylglycidate; ethyl 3-methyl-3-phenylglycidate;

nitrogen-containing aromatic compounds such as, for example, 2,4,6-trinitro-1,3-dimethyl-5-tert-butylbenzene; 3,5-dinitro-2,6-dimethyl-4-tert-butylacetophenone; cinnamonitrile; 5-phenyl-3-methyl-2-pentenonitrile; 5-phenyl-3-methylpentanonitrile; methyl anthranilate; methyl N-methylanthranilate; Schiff bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; indole; skatole; 2-methoxy-3-isopropylpyrazine; 2-isobutyl-3-methoxypyrazine;

phenols, phenyl ethers and phenyl esters such as, for example, estragole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresylphenyl acetate;

heterocyclic compounds such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

and also stereoisomers, enantiomers, positional isomers, diastereomers, cis/trans isomers or epimers (which are not explicitly mentioned here) of these substances.

In a preferred embodiment, the fragrance composition or the aroma composition is a liquid or solid aroma composition.

The present invention similarly further provides for the use of the preparation according to the invention as fine fragrance or perfume.

The present invention further provides a substance mixture containing (a) one, two or more compounds selected from the group consisting of
 (a1) alcohol monoterpenes of formula (I)

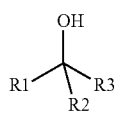

(I)

where
 R1 is H or methyl, R2 is H or C$_2$-alkenyl, and R3 is a linear or branched, saturated or unsaturated hydrocarbon radical having 4 to 10 carbon atoms, and also the enantiomers, diastereomers, racemates, solvates and physiologically compatible salts thereof,
and/or
 (a2) bicyclic epoxy monoterpenes,
(b) at least two lactones of formula (II)

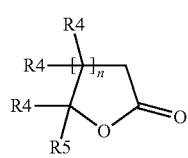

(II)

where
R4 is H or methyl, R5 is a linear or branched, saturated or unsaturated hydrocarbon radical having 2 to 10 carbon atoms and n is the numbers 1 or 2, and also the enantiomers, diastereomers and racemates thereof, (c) one, two or more solvents selected from the group consisting of
 (c1) ethanol and/or
 (c2) one, two or more solvents selected from the group consisting of water, dipropylene glycol (DPG), diethyl phthalate (DEP), propylene glycol (PG), isopropyl myristate (IPM), isopropyl palmitate (IPP), triethyl citrate (TEC), triacetin (TRI), 1,2-propanediol, 1,3-propanediol, propanethiol, pentanediol, hexanediol, octanediol, decanediol (SymClariol®), dodecanol, 4-hydroxyacetophenone (SymSave® H), glycerol, butylene glycol, pentylene glycol, hexylene glycol, decylene glycol, propylene carbonate, butylene carbonate, glycerol carbonate, 2-benzylheptanol, lauryl alcohol, trimethyl hydroxypentyl isobutyrate, glyceryl caprylate, ethylhexylglycerin, benzyl benzoate (BB),
and optionally
(d) further aroma substances or fragrances selected from the group consisting of 3-phenylbutanal (trifernal), acetylmethylcarbinol, anethole, anisyl acetate, dihydroeugenol, linalyl formate, 2-methyldecanal, 2-benzyl-2-methylbut-3-enenitrile (Citrowanil® B), 3-hexenyl acetate, styralyl acetate, belanis, citronellal, cinnamyl acetate, rhubafuran, beta-ionone, anther, prenyl acetate, 2-phenylpropanal, 4-(4-hydroxyphenyl)butan-2-one) (Frambinon®, ethyl phenoxyacetate, isoraldeine, gamma-terpinene, limonene, neocyclocitral, methyl lavender ketone, styralyl propionate, phenethyl propionate, limonenal, 4-isopentylcyclohexanol) (Symrose®, 4-methyl-2-phenyl-3,6-dihydro-2H-pyran/4-methylene-2-phenyltetrahydropyran (Rosyrane super), hydrocitronitrile, phenoxanol, isoamyl phenylacetate, damascone, silvial, nectaryl, ambroxide, acetyl pyrazine, trimethyl pyrazine, isoamyl acetate, paracresyl methyl ether, filbertone, cyclohexyl acetate, heliotropin, acetophenone, anisaldehyde, para-methyl acetophenone, veratraldehyde, methyl anisate and vertoprenal.

It was found that, surprisingly, the substance mixture according to the invention in very low concentrations is capable of reducing or masking the perceived intensity of unpleasant and undesired off-notes in a multiplicity of oleochemical formulations, especially odor or aroma off-notes which are perceived by the test subjects as pungent, irritating, oxidized, acrid, rancid, fatty, animalistic, goat, fermented, musty, herbaceous and vomit, as demonstrated by the experimental data in Table 2 of Example 1.

Furthermore, it was found that, surprisingly, the substance mixture according to the invention further develops its action even during the phases of utilization, even after rinse-off of the substance mixture according to the invention or of the preparation containing the substance mixture according to the invention, as demonstrated by the experimental data in Tables 3 and 4 of Example 1. For instance, it was found that, surprisingly, preparations containing the substance mixture according to the invention bring about the covering of undesired off-notes even during use, i.e., when washing hands or hair and after rinse-off, in contrast to normal perfuming agents or aromatization agents at this dosage.

It became apparent that the substance mixture according to the invention is particularly suitable for masking, covering or reducing undesired off-notes which are caused by aldehydes of formula (III)

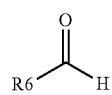

(III)

where R6 is a saturated or unsaturated, linear hydrocarbon radical, preferably having a chain length of 3 to 10 carbon atoms,
and/or free fatty acids of formula (IV)

(IV)

where R7 is a linear or branched, saturated hydrocarbon radical, preferably a chain length of 3 to 12 carbon atoms.

It was found that, surprisingly, the substance mixture according to the invention, or the combination of component (a), (b) and (c) and optionally component (d), has a synergistic action. It thus became apparent that the combination according to the invention covers the undesired off-notes distinctly better than the substances of group (a), (b) and (c) and optionally of group (d) alone (synergistic action) and cover in combination the off-notes caused by the aldehydes of formula (III) or by aldehydes of formula (III) and fatty acids of formula (IV) better than the groups on their own, as demonstrated by the experimental data in Table 2 of Example 1.

The off-notes caused by aldehydes of formula (III) and fatty acids of formula (IV) are described or perceived by the test subjects as pungent, irritating, oxidized, acrid, rancid, fatty, animalistic, goat, fermented, musty, herbaceous and vomit.

It became apparent that the substance mixture according to the invention is particularly suitable for masking, covering or reducing undesired off-notes which by aldehydes of formula (III) and/or free fatty acids of formula (IV), wherein the aldehydes of formula (III) are selected from the group consisting of hexanal, heptanal, octanal, nonanal, decanal, hexenal, heptenal, octenal, nonenal, decenal, undecenal, dodecenal, hexadienal, heptadienal, octadienal, nonadienal, decadienal, undecadienal, dodecadienal, octatrienal, nonatrienal, decatrienal, undecatrienal, dodecatrienal, especially preferably hexanal, octanal, nonanal, hexenal, heptenal, octenal, heptadienal, octadienal, decadienal and decatrienal,
and
the free fatty acids of formula (IV) are selected from the group consisting of butanoic acid, pentanoic acid, isovaleric acid, hexanoic acid, heptanoic acid, octanoic acid, nonanoic acid, decanoic acid, undecanoic acid and dodecanoic acid, especially preferably hexanoic acid, octanoic acid and decanoic acid.

The present invention therefore further provides for the use of the substance mixture according to the invention for the reduction and/or masking of undesired odor or aroma off-notes in oleochemical preparations.

The present invention therefore further provides for the use of the substance mixture according to the invention for the reduction and/or masking of undesired odor or aroma off-notes in oleochemical preparations, especially of undesired off-notes which are caused by aldehydes of formula (III) and/or free fatty acids of formula (IV) as defined above.

In a preferred embodiment, the substance mixture according to the invention contains at least two, three or four substances of group (a).

It became apparent that the compounds linalool, geraniol, freesiol and nerolidol and also the enantiomers, diastereomers, racemates, solvates and physiologically compatible salts thereof are particularly suitable as component (a1) for masking the undesired off-notes of the aldehydes of formula (III) and/or the free fatty acids of formula (IV), especially the undesired off-notes by the above-mentioned specific aldehydes of formula (III) and/or the specific free fatty acids of formula (IV).

In a preferred embodiment, the bicyclic epoxy monoterpenes (component (a2)) are epoxy-p-menthane derivatives. Similarly, it became apparent that the compounds 1,4-cineole and 1,8-cineole are particularly suitable as component (a2) for masking the undesired off-notes of the aldehydes of formula (III) and/or the free fatty acids of formula (IV), especially the undesired off-notes by the abovementioned specific aldehydes of formula (III) and/or the specific free fatty acids of formula (IV).

In a preferred embodiment, the substance mixture according to the invention contains at least one compound of group (a1) and at least one compound of group (a2), wherein the compounds of group (a1) are selected from the group consisting of linalool, geraniol, freesiol and nerolidol and also the enantiomers, diastereomers, racemates, solvates and physiologically compatible salts thereof and the compounds of group (a2) are selected from the group consisting of compounds 1,4-cineole and 1,8-cineole.

In a further preferred embodiment of the substance mixture according to the invention, components (a1) and (a2) are in a weight ratio of about 100:1 to about 1:100, preferably about 50:1 to about 1:50 and especially preferably of about 20:1 to about 1:20.

With regard to component (b), the substance mixture according to the invention contains at least two, optionally three or four, lactones of formula (II).

In a preferred embodiment, the substance mixture according to the invention contains at least two lactones—optionally three or four—selected from the group consisting of the lactones of formula (II) and also the enantiomers, diastereomers and racemates thereof, wherein R4 is H, R5 is linear and saturated hydrocarbon radicals having 2 to 10 carbon atoms, n is the numbers 1 or 2, particularly preferably where R4=H and R5=linear and saturated hydrocarbon radicals having 2 to 8 carbon atoms and n=1 or 2.

In a further preferred embodiment, the substance mixture according to the invention contains at least two lactones—optionally three or four—selected from the group consisting of gamma-dodecalactone, gamma-decalactone, gamma-undecalactone, delta-decalactone, delta-dodecalactone, 4-methyl-gamma-nonalactone, 3-methyl-gamma-decalactone, gamma-nonalactone, delta-nonalactone, gamma-octalactone, delta-octalactone, gamma-heptalactone, delta-heptalactone, gamma-hexalactone and delta-hexalactone, preferably gamma-dodecalactone, gamma-decalactone, delta-decalactone and delta-dodecalactone.

It became apparent that gamma-decalactone, delta-decalactone, gamma-dodecalactone and delta-dodecalactone are particularly suitable as component (b) for masking the undesired off-notes of the aldehydes of formula (III) and/or of the free fatty acids of formula (IV), especially the undesired off-notes by the abovementioned specific aldehydes of formula (III) and/or the specific free fatty acids of formula (IV).

With regard to component (c), it became apparent that the combination of ethanol with one, two or more solvents selected from the group consisting of dipropylene glycol (DPG), diethyl phthalate (DEP), propylene glycol (PG), isopropyl myristate (IPM), isopropyl palmitate (IPP), triethyl citrate (TEC), triacetin (TRI), 1,2-propanediol, 1,3-propanediol, propanethiol, pentanediol, hexanediol, octanediol, decanediol (SymClariol®), dodecanol, 4-hydroxyacetophenone (SymSave® H), glycerol, butylene glycol, pentylene glycol, hexylene glycol, decylene glycol, propylene carbonate, butylene carbonate, glycerol carbonate, 2-benzylheptanol, lauryl alcohol, trimethyl hydroxypentyl isobutyrate, glyceryl caprylate, ethylhexylglycerin, benzyl benzoate (BB) and especially selected from the group consisting of dipropylene glycol (DPG), diethyl phthalate (DEP), propylene glycol (PG), isopropyl myristate (IPM), isopropyl palmitate (IPP), triethyl citrate (TEC), triacetin (TRI), 1,2-propanediol, 1,3-propanediol, propanethiol, pentanediol, hexanediol, octanediol, decanediol (SymClariol®), dodecanol, 4-hydroxyacetophenone (SymSave® H), benzyl benzoate (BB) is advantageous for specific uses, particularly with respect to the further processing of the substance mixture according to the invention in some end products. Accordingly, the substance mixture according to the invention can contain at least two, three or four of the abovementioned solvents.

With regard to the optional component (d), it became apparent that the combination of at least two, preferably at least three or four, of the aroma substances or fragrances of group (d) is advantageous for specific uses, particularly with respect to the further processing of the substance mixture according to the invention in some end products. Accordingly, the substance mixture according to the invention can contain at least two, three or four of the of the aroma substances or fragrances of group (d).

In a further preferred embodiment, the substance mixture according to the invention contains one or more aroma substances or fragrances of group (d), these being selected from the group of 3-phenylbutanal (trifernal), acetylmethylcarbinol, 2-methyldecanal, 2-benzyl-2-methylbut-3-enenitrile (Citrowanil® B), 3-hexenyl acetate, styralyl acetate, rhubafuran, anther, prenyl acetate, styralyl propionate, isoamyl phenylacetate, beta-damascone, isoamyl acetate, citronellol and cyclohexyl acetate.

In a further preferred embodiment, the substance mixture according to the invention is characterized in that it contains
(i) 0.0000001% to 80% by weight of component (a),
(ii) 0.0000001% to 80% by weight of component (b),
(iii) 0.0000001% to 98% by weight of component (c), preferably 0.0000001% to 80% by weight, particularly preferably 0.0000001% to 75% by weight, and especially preferably 0.0000001% to 65% by weight,
(iv) 0% to 80% by weight of component (d),
with the proviso that the quantitative data with optionally further ingredients add up to 100% by weight, based on the total weight of the substance mixture.

In a further preferred embodiment, the substance mixture according to the invention is characterized in that it contains
(i) 0.00001% to 50% by weight of component (a),
(ii) 0.00001% to 80% by weight of component (b),
(iii) 0.001% to 95% by weight of component (c), preferably 0.001% to 80% by weight, particularly preferably 0.001% to 75% by weight, and especially preferably 0.001% to 65% by weight,
(iv) 0 to 70% by weight of component (d),
with the proviso that the quantitative data with optionally further ingredients add up to 100% by weight, based on the total weight of the substance mixture.

In a further preferred embodiment, the substance mixture according to the invention is characterized in that it contains
(i) 0.001% to 40% by weight of component (a),
(ii) 0.001% to 80% by weight of component (b),
(iii) 0.01% to 95% by weight of component (c), preferably 0.01% to 80% by weight, particularly preferably 0.01% to 75% by weight, and especially preferably 0.01% to 65% by weight,
(iv) 0% to 60% by weight of component (d),
with the proviso that the quantitative data with optionally further ingredients add up to 100% by weight, based on the total weight of the substance mixture.

In a further preferred embodiment, the substance mixture according to the invention is characterized in that it contains
(i) 0.1% to 40% by weight of component (a),
(ii) 0.1% to 80% by weight of component (b),
(iii) 0.1% to 90% by weight of component (c), preferably 0.1% to 80% by weight, particularly preferably 0.1% to 75% by weight, and especially preferably 0.1% to 65% by weight,
(iv) 0% to 50% by weight of component (d),
with the proviso that the quantitative data with optionally further ingredients add up to 100% by weight, based on the total weight of the substance mixture.

It became apparent that ethanol has a positive influence not only on the desired masking action, but also on the further processing of the substance mixture according to the invention in end products.

In this context, the amount of ethanol in a further embodiment of the substance mixture according to the invention is ≤30% by weight, further preferably ≤20% by weight, preferably ≤15% by weight, particularly preferably ≤10% by weight, based on the total weight of the substance mixture.

In a further preferred embodiment, the substance mixture according to the invention is characterized in that it contains
(i) 0.0000001% to 80% by weight of component (a),
(ii) 0.0000001% to 80% by weight of component (b),
(iii) 0.0000001% to 98% by weight of component (c), preferably 0.0000001% to 80% by weight, particularly preferably 0.0000001% to 75% by weight, and especially preferably 0.0000001% to 65% by weight,
(iv) 0% to 80% by weight of component (d),
with the proviso that
the amount of ethanol (component c1)) is ≤30% by weight, further preferably ≤20% by weight, preferably ≤15% by weight, particularly preferably ≤10% by weight, based on the total weight of the substance mixture,
and
the quantitative data with optionally further ingredients add up to 100% by weight, based on the total weight of the substance mixture.

In a further preferred embodiment, the substance mixture according to the invention is characterized in that it contains
(i) 0.00001% to 50% by weight of component (a),
(ii) 0.00001% to 80% by weight of component (b),
(iii) 0.001% to 95% by weight of component (c), preferably 0.001% to 80% by weight, particularly preferably 0.001% to 75% by weight, and especially preferably 0.001% to 65% by weight,
(iv) 0% to 70% by weight of component (d),
with the proviso that
the amount of ethanol (component c1)) is ≤30% by weight, further preferably ≤20% by weight, preferably ≤15% by weight, particularly preferably ≤10% by weight, based on the total weight of the substance mixture,
and
the quantitative data with optionally further ingredients add up to 100% by weight, based on the total weight of the substance mixture.

In a further preferred embodiment, the substance mixture according to the invention is characterized in that it contains (i) 0.001% to 40% by weight of component (a),
(ii) 0.001% to 80% by weight of component (b),
(iii) 0.01% to 95% by weight of component (c), preferably 0.01% to 80% by weight, particularly preferably 0.01% to 75% by weight, and especially preferably 0.01% to 65% by weight,
(iv) 0% to 60% by weight of component (d),
with the proviso that
the amount of ethanol (component c1)) is ≤30% by weight, further preferably ≤20% by weight, preferably ≤15% by weight, particularly preferably ≤10% by weight, based on the total weight of the substance mixture,
and
the quantitative data with optionally further ingredients add up to 100% by weight, based on the total weight of the substance mixture.

In a further preferred embodiment, the substance mixture according to the invention is characterized in that it contains
(i) 0.1% to 40% by weight of component (a),
(ii) 0.1% to 80% by weight of component (b),
(iii) 0.1% to 90% by weight of component (c), preferably 0.1% to 80% by weight, particularly preferably 0.1% to 75% by weight, and especially preferably 0.1% to 65% by weight,
(iv) 0% to 50% by weight of component (d),
with the proviso that
the amount of ethanol (component c1)) is ≤30% by weight, further preferably ≤20% by weight, preferably ≤15% by weight, particularly preferably ≤10% by weight, based on the total weight of the substance mixture,
and
the quantitative data with optionally further ingredients add up to 100% by weight, based on the total weight of the substance mixture.

In a further preferred embodiment of the substance mixture according to the invention, components (a) and (b) are in a weight ratio of about 100:1 to about 1:100, preferably about 50:1 to about 1:50 and especially preferably of about 1:20 to about 20:1.

A further embodiment of the substance mixture according to the invention contains component (a+b) and (c) in the weight ratio of about 100:1 to 1:100, particularly preferably about 50:1 to 1:50 and especially preferably about 30:1 to 1:30.

In a preferred embodiment, the substance mixture according to the invention is present as a liquid mixture. However, this can be converted into a solid preparation, for example by spray-drying.

The present invention therefore further provides a method for producing the abovementioned substance mixture according to the invention, comprising the steps of:
i) mixing (a), (b), (c) and optionally (d), wherein component (a) to (d) can be present in the form of solids, solutions, extracts, aqueous extracts and enriched preparations or concentrates, for example by distillation, chromatography or by the method described in EP 2 075321 B1,
and optionally
ii) the substance mixture thus obtained subsequently subjected to a spray-drying procedure.

In the context of the present invention, the substance mixture according to the invention can be combined with additional fragrances or aroma substances.

The present invention therefore further provides a fragrance or aroma composition containing the substance mixture according to the invention in combination with additional fragrances or aroma substances of group (e) that can be incorporated in oleochemical preparations or end products.

With regard to the additional fragrances or aroma substances of group (e), the above remarks apply.

In a preferred embodiment, the fragrance composition or the aroma composition is a liquid or solid aroma composition.

The present invention therefore further provides a method for producing the abovementioned fragrance or aroma composition, comprising the steps of:
i) mixing (a), (b), (c) and optionally (d), wherein component (a) to (d) can be present in the form of solids, solutions, extracts, aqueous extracts and enriched preparations or concentrates, for example by distillation, chromatography or by the method described in EP 2 075321 B1,
and optionally
ii) the mixture thus obtained subsequently subjected to a spray-drying procedure.

The present invention therefore further provides for the use of the of the abovementioned fragrance or aroma composition for the reduction and/or masking of undesired off-notes in oleochemical preparations, especially of undesired off-notes which are caused by aldehydes of formula (III) and/or free fatty acids of formula (IV) as defined above.

In the context of the present invention, the substance mixture according to the invention can be used in any desired products in which the aim is to mask unpleasant odor or aroma notes caused especially by aldehydes of formula (III) and/or the free fatty acids of formula (IV) or to replace them with aroma or fragrance notes perceived as pleasant notes. Typical examples of product groups in which the substance mixture according to the invention can be used are, for example, soap bases, laundry detergents, dishwashing liquids and cleaners and also cosmetic preparations. Preferably, the substance mixture according to the invention is used in amounts of 0.0001% to 3% by weight, preferably 0.001% to 1.5% by weight, particularly preferably 0.01% to 1.2% by weight, especially preferably 0.01% to 1% by weight, based on the preparation or end product.

Therefore, the present invention further provides preparations, especially oleochemical preparations, or end products which contain the substance mixture according to the invention or the abovementioned fragrance or aroma composition containing the substance mixture according to the invention and additional fragrances or aroma substances of group (e).

Consequently, the present invention further provides preparations containing
(i) the abovementioned substance mixtures according to the invention,
and
(ii) aldehydes of formula (III)
and/or
(iii) free fatty acids of formula (IV).

In a preferred embodiment, the preparations are oleochemical preparations.

In a preferred embodiment, the oleochemical preparations or end products are selected selected from the group consisting of cleaner, laundry detergent, air freshener, candles, dishwashing liquid, fabric softener, skin cream, lip care product, makeup remover, hair conditioner, lotion, shampoo, shower gel and soap and the solid and liquid embodiments thereof, particularly preferably shampoo, shower gel, soap and the solid and liquid embodiments thereof.

Therefore, the present invention further provides for the use of the substance mixture according to the invention or the abovementioned fragrance or aroma composition containing the substance mixture according to the invention and additional fragrances or aroma substances of group (d) for the reduction and/or masking of undesired odor or aroma off-notes in oleochemical preparations, especially of undesired off-notes which are caused by aldehydes of formula (III) and/or free fatty acids of formula (IV) as defined above, the oleochemical preparations being selected from the group consisting of cleaner, laundry detergent, air freshener, candles, dishwashing liquid, fabric softener, skin cream, lip care product, makeup remover, hair conditioner, lotion, shampoo, shower gel and soap and the solid and liquid embodiments thereof.

The invention further provides preparations containing the abovementioned inventive substance mixtures or fragrance or aroma compositions and aldehydes of formula (III) and/or free fatty acids of formula (IV).

The preparations can the end products in amounts of 0.0001% to 3% by weight, preferably 0.001% to 1.5% by weight, particularly preferably 0.01% to 1.2% by weight, especially preferably 0.01% to 1% by weight, based on the end product.

In a further embodiment, the preparations contain component (a) and (b), or (a) and (c) or (a) and (c+b), in the weight ratio of 1:0.00001 to 1:120, preferably 1:0.001 to 1:100, especially 1:0.01 to 1:50.

The preparations are used in end products selected are selected from the group consisting of cleaner, laundry detergent, air freshener, candles, dishwashing liquid, fabric softener, skin cream, lip care product, makeup remover, hair conditioner, lotion, shampoo, shower gel and soap and the solid and liquid embodiments thereof, preferably soap and the solid and liquid embodiments thereof, shampoo and shower gel, and particularly preferably soap and the solid and liquid embodiments thereof.

Similarly, the present invention further provides for the use of the substance mixture according to the invention or of the abovementioned fragrance or aroma composition as fine fragrance or perfume.

INDUSTRIAL APPLICABILITY

According to the present invention, it is possible to produce substance mixtures, fragrance or aroma compositions and preparations which can be used for the reduction and/or masking of undesired off-notes in preparations, especially in oleochemical preparations.

The invention further provides for the use of the abovementioned substance mixtures, aroma compositions and preparations for the production of intermediate products and end products selected are selected from the group consisting of perfume, cleaner, laundry detergent, air freshener, candles, dishwashing liquid, fabric softener, skin cream, lip care product, makeup remover, hair conditioner, lotion, shampoo, shower gel and soap and the solid and liquid embodiments thereof, preferably soap and the solid and liquid embodiments thereof, shampoo and shower gel, and particularly preferably soap and the solid and liquid embodiments thereof.

EXAMPLES

The present invention will be more easily understandable with reference to the following examples. However, said examples serve merely to illustrate the invention and cannot be interpreted as having a limiting effect with respect to the scope of protection of the invention.

Unless otherwise indicated, all data are based on weight.

Example 1—Soap Bar

TABLE 1

Composition of soap bar

| | Constituent | INCI | Soap 1 wt % | Soap 2 wt % | Soap 3 wt % | Soap 4 wt % | Soap 5 wt % | Soap 6 wt % | Soap 7 wt % |
|---|---|---|---|---|---|---|---|---|---|
| Phase A | Base soap | Sodium tallowate, sodium cocoate, sodium palm kernel fatty acid salt | 97.5 | 97.5 | 97.5 | 97.5 | 97.5 | 97.5 | 97.5 |
| | Water | Water | 0.5000 | 0.5000 | 0.5000 | 0.5000 | 0.5000 | 0.5000 | 0.5000 |
| | Titanium dioxide | Titanium dioxide | 1.0000 | 1.0000 | 1.0000 | 1.0000 | 1.0000 | 1.0000 | 1.0000 |
| Phase B | DPG | Dipropylene glycol | 1.0000 | 0.9750 | 0.9975 | 0.9960 | 0.9685 | 0.9500 | 0.9935 |
| | gamma-Dodecalactone | | — | 0.0150 | — | — | 0.0150 | 0.0150 | — |
| | gamma-Decalactone | | — | 0.0100 | — | — | 0.0100 | 0.0100 | — |
| | Ethanol | | — | — | 0.0025 | — | 0.0025 | 0.0025 | 0.0025 |
| | Geraniol | | — | — | — | 0.0040 | 0.0040 | — | 0.0040 |
| | Limonene | | — | — | — | — | — | 0.0225 | — |
| | Total | | 100.0000 | 100.0000 | 100.0000 | 100.0000 | 100.0000 | 100.0000 | 100.0000 |

To produce soap sample 1 to 7, phase B, which corresponds to inventive substance mixture 1, is premixed. The constituents of phase A and the premixed phase B are mixed in a kneader. The mass obtained is shaped into bars using an extruder. Thereafter, the bars were conditioned at room temperature for 7 days.

Phases B of soap bars 1-4 and 6-7 are not according to the invention, since they contain the not all required components (a) to (c) according to the present invention. Thus, phase B of soap bar 1 contains only component (c), phase B of soap bar 2 contains components (b) and (c), phase B of soap bar 3 contains component (c), phase B of soap bar 4 contains component (a) and (c), phase B of soap bar 6 contains component (b), (c) and (e), and soap bar 7 contains component (a) and (c).

Phase B of soap bar 5 is an inventive substance mixture which comprises the required component (a) to (c).

The conditioned bars were coded and sensorially assessed by an expert panel of 15 people. This involved measuring the perceived total intensity and the perceived intensity of undesired off-notes and also a description of the olfactory impression. The measured values were compared with the values of soap specimen 1 and the percentages of off-note intensity, based on soap bar 1, were calculated.

The sensory measurements of soap bars 1 to 7 are put together in Table 2:

TABLE 2

Results of the sensory measurements of soap bars 1 to 7

|  | Soap 1 | Soap 2 | Soap 3 | Soap 4 | Soap 5 | Soap 6 | Soap 7 |
|---|---|---|---|---|---|---|---|
| Total intensity | 4.3 | 4.1 | 4.3 | 4.1 | 5.1 | 4.3 | 4.1 |
| Off-note intensity | 4.3 | 3.0 | 4.2 | 3.3 | 0.9 | 3.3 | 3.3 |
| Reduction in off-note intensity [%] in comparison with soap 1 |  | 30 | 2 | 23 | 79 | 23 | 23 |
| Description | Fatty, oxidized, rancid, pungent, irritating | Fatty, creamy, slightly oxidized, pungent | Fatty, oxidized, rancid, pungent, irritating | Fatty, rancid, slightly oxidized, flowery, irritating | Fresh, flowery, soft, creamy | Fatty, creamy, oxidized, pungent, irritating | Fatty, rancid, slightly oxidized, flowery, irritating |

Furthermore, the olfactory impressions of the different soap bar 1 to 7 were measured over the phases of utilization. To this end, one hand was washed with soap bar 1 and the other hand was washed with a different soap bar. The expert panel then assessed in each case the hand lathered with the soap and then the damp hand rinsed with water, with the perceived total intensity, the off-note intensity and also a description being ascertained again. The sensory evaluation is put together in Tables 3 and 4:

TABLE 3

Results of the sensory measurements of lathered hands for soap bars 1 to 7

|  | Soap 1 | Soap 2 | Soap 3 | Soap 4 | Soap 5 | Soap 6 | Soap 7 |
|---|---|---|---|---|---|---|---|
| Total intensity | 3.5 | 3.8 | 3.6 | 3.9 | 4.3 | 3.6 | 3.9 |
| Off-note intensity | 3.1 | 2.4 | 3.0 | 2.5 | 1.1 | 2.5 | 2.5 |
| Reduction in off-note intensity [%] in comparison with soap 1 |  | 23 | 3 | 19 | 65 | 19 | 19 |
| Description | Irritating, fatty, oxidized | Creamy, fatty, pungent | Fatty, oxidized, irritating, pungent | Fatty, flowery, irritating, slightly oxidized | Fresh, flowery, soft, creamy | Fatty, creamy, oxidized, irritating, pungent | Fatty, flowery, irritating, slightly oxidized |

TABLE 4

Results of the sensory measurements of rinsed, damp hands for soap bars 1 to 7

|  | Soap 1 | Soap 2 | Soap 3 | Soap 4 | Soap 5 | Soap 6 | Soap 7 |
|---|---|---|---|---|---|---|---|
| Total intensity | 2.4 | 2.8 | 2.4 | 2.7 | 3.9 | 2.7 | 2.7 |
| Off-note intensity | 2.1 | 1.6 | 2.0 | 1.7 | 0.8 | 1.6 | 1.6 |

TABLE 4-continued

Results of the sensory measurements of rinsed, damp hands for soap bars 1 to 7

|  | Soap 1 | Soap 2 | Soap 3 | Soap 4 | Soap 5 | Soap 6 | Soap 7 |
|---|---|---|---|---|---|---|---|
| Reduction in off-note intensity [%] in comparison with soap 1 |  | 24 | 5 | 19 | 62 | 24 | 24 |
| Description | Irritating, musty, oxidized, fermented | Creamy, slightly oxidized | Oxidized, irritating, fermented, slightly musty | Flowery, irritating, slightly oxidized | Soft, neutral, flowery, creamy | Irritating, creamy, slightly oxidized | Flowery, slightly oxidized |

The results show that the combination of geraniol (component (a)), lactones (component (b)) and the solvents EtOH and DPG (component (c)) in the inventive soap bar 5 has distinctly lower values in the perceived off-note intensity than these substances alone. This synergistic effect was found in all phases of utilization and shows that the substances are active for longer than other substances. Furthermore, this effect occurs even at low concentrations or dosages.

Example 2

Further examples of the substance mixture according to the invention are put together in Tables 5 to 6:

TABLE 5

Example substance mixture 2

| Substance | wt % |
|---|---|
| Dodecalactone-gamma | 30.0 |
| Decalactone-gamma | 20.0 |
| Decalactone-delta | 20.0 |
| Ethanol | 6.0 |
| 1,8-Cineole | 8.0 |
| 1,4-Cineole | 1.0 |
| Freesiol | 15.0 |
| Total | 100.0 |

TABLE 6

Example substance mixture 3

| Substance | wt % |
|---|---|
| Dodecalactone-gamma | 20.0 |
| Decalactone-gamma | 20.0 |
| Decalactone-delta | 20.0 |
| Undecalactone-gamma | 20.0 |
| Ethanol | 4.0 |
| Geraniol | 8.0 |
| Linalool | 8.0 |
| Total | 100.0 |

Example 3

Examples of mixtures (M1) in combination with further aroma substances or fragrances as fragrance/perfume or aroma/flavor are put together in Tables 7 to 12:

TABLE 7

Example mixture 4

| Substance | wt % |
|---|---|
| 1,4-Cineole | 0.115 |
| 2-Methyldecanal | 0.022 |
| 2-Phenyl acetate | 0.041 |
| 3-Hexenyl acetate | 0.021 |
| 3-Methyldecalactone-gamma | 0.102 |
| Acetophenone | 0.002 |
| Agrumex HC | 3.874 |
| Anisaldehyde | 0.325 |
| Citronellal | 0.004 |
| Citronellol | 0.574 |
| Citrowanil ® B | 0.223 |
| Cyclohexyl acetate | 0.119 |
| Damascone | 0.088 |
| Decalactone-delta | 0.314 |
| Decalactone-gamma | 0.455 |
| Dihydromyrcenol | 5.987 |
| Dodecalactone-delta | 0.054 |
| Dodecalactone-gamma | 1.187 |
| DPG | 58.503 |
| Ethanol | 1.215 |
| Ethyl phenoxyacetate | 0.002 |
| Ethylvanillin | 0.0001 |
| Filbertone | 0.0001 |
| Freesiol | 0.341 |
| Geraniol | 5.100 |
| Globalide ® | 0.145 |
| Heliotropin | 0.771 |
| Heptalactone-gamma | 0.013 |
| Herbyl formate | 3.111 |
| Ionone-beta | 3.312 |
| Isoamyl acetate | 0.071 |
| Isoamyl phenylacetate | 0.208 |
| Limonenal | 0.021 |
| Linalool | 1.210 |
| Linalyl acetate | 2.978 |
| Linalyl formate | 0.232 |
| Methylacetophenone-para | 0.002 |
| Methyl anisate | 0.0330 |
| Methyl lavender ketone | 0.038 |
| Nectaryl | 0.018 |
| Neocyclocitral | 0.011 |
| Nerolidol | 0.097 |
| Nonalatone-gamma | 0.045 |
| Octalactone-gamma | 0.025 |
| Orange oil/limonene | 6.510 |
| Phenoxanol | 0.014 |
| Phenethyl alcohol | 0.748 |
| Phenethyl propionate | 0.101 |

TABLE 7-continued

Example mixture 4

| Substance | wt % |
|---|---|
| Rhubafuran | 0.004 |
| Styralyl propionate | 0.021 |
| Styralyl acetate | 0.190 |
| Terpinene-gamma | 1.071 |
| Undecalactone-gamma | 0.321 |
| Vanillin | 0.0001 |
| Veratraldehyde | 0.003 |
| Vertoprenal | 0.008 |
| Total | 100.0000 |

TABLE 8

Example mixture 5

| Substance | wt % |
|---|---|
| 1,4-Cineole | 0.011 |
| 1,8-Cineole | 0.312 |
| 2-Phenylpropanal | 0.024 |
| 3-Methyldecalactone-gamma | 0.113 |
| Acetylmethylcarbinol | 0.001 |
| Agrumex HC | 2.300 |
| Ambroxide | 0.001 |
| Amyl salicylate | 1.000 |
| Anethole | 0.059 |
| Anisaldehyde | 0.578 |
| Anisyl acetate | 0.012 |
| Anther | 0.112 |
| Belanis | 0.026 |
| Benzyl acetate | 9.000 |
| Benzyl salicylate | 3.000 |
| Cinnamyl acetate | 0.167 |
| Citronellol | 1.000 |
| Citrowanil ® B | 0.258 |
| Cresyl methyl ether-para | 0.257 |
| Damascone | 0.005 |
| Decalactone-delta | 0.010 |
| Decalactone-gamma | 0.553 |
| Dihydroeugenol | 0.089 |
| Dihydromyrcenol | 4.000 |
| Dodecalactone-delta | 0.100 |
| Limonenal | 0.100 |
| Dodecalactone-gamma | 0.352 |
| DPG | 45.212 |
| Ethanol | 5.000 |
| Frambinon ® | 0.010 |
| Geraniol | 3.200 |
| Heliotropin | 0.080 |
| Heptalactone-gamma | 0.014 |
| Herbyl propionate | 4.700 |
| Hydrocitronitrile | 0.014 |
| Ionone-beta | 4.600 |
| Iso E Super | 1.000 |
| Isoraldeine | 1.030 |
| Linalool | 1.780 |
| Linalyl acetate | 4.780 |
| Linalyl formate | 3.140 |
| Octalactone-gamma | 0.081 |
| Orange oil/limonene | 1.287 |
| Rosyrane super | 0.015 |
| Silvial | 0.170 |
| Styralyl acetate | 0.198 |
| Symrose ® | 0.020 |
| Terpinene-gamma | 0.114 |
| Trifernal | 0.010 |
| Trimethylpyrazine | 0.0001 |
| Undecalactone | 0.105 |
| Vanillin | 0.0001 |
| Total | 100.0000 |

TABLE 9

Example mixture 6

| Substance | wt % |
|---|---|
| Dodecalactone-gamma | 2.0 |
| Decalactone-delta | 1.0 |
| Ethanol | 5.0 |
| 1,8-Cineole | 24.0 |
| 1,4-Cineole | 5.0 |
| L-Menthol | 35.0 |
| Anethole | 28.0 |
| Total | 100.0 |

TABLE 10

Example substance mixture 7

| Substance | wt % |
|---|---|
| Dodecalactone-gamma | 1.5 |
| Decalactone-gamma | 1.5 |
| Anethole | 7.0 |
| Peppermint oil, *Mentha piperita*, type Willamette | 18.0 |
| Peppermint oil, *Mentha arvensis*, rectified | 18.0 |
| Ethanol | 1.0 |
| 1,8-Cineole | 5.0 |
| 1,4-Cineole | 2.0 |
| L-Menthol | 45.0 |
| Linalool | 1.0 |
| Total | 100.0 |

TABLE 11

Example substance mixture 8

| Substance | wt % |
|---|---|
| Dodecalactone-gamma | 5.0 |
| Decalactone-delta | 5.0 |
| Ethanol | 2.5 |
| 1,4-Cineole | 1.0 |
| Gernaniol | 0.5 |
| Linalool | 1.0 |
| Vanillin, 10% in DPG | 3.0 |
| Orange oil, Brazilian | 65.0 |
| Glycerol | 5.0 |
| Lemon oil terpene | 12.0 |
| Total | 100.0 |

TABLE 12

Example mixture 9

| Substance | wt % |
|---|---|
| 1,4-CINEOLE | 0.0200 |
| DECALACTONE-DELTA | 0.0030 |
| DECALACTONE-GAMMA | 0.0030 |
| DODECALACTONE-DELTA | 0.0100 |
| DODECANLACTONE-GAMMA | 0.0100 |
| ETHANOL | 1.7500 |
| FREESIOL | 0.2000 |
| GERANIOL | 0.0040 |
| ROSEMARY OIL | 0.5000 |
| DIHYDROMYRCENOL | 11.0000 |
| HERBAFLORATE (ACETIC ACID TRICYCLO[5.2.1.0]-4-DECEN-8-YL ESTER) | 5.0000 |
| HEXYL CINNAMALDEHYDE ALPHA | 10.0000 |

TABLE 12-continued

Example mixture 9

| Substance | wt % |
|---|---|
| COUMARIN | 1.0000 |
| DIPHENYL OXIDE | 5.0000 |
| LILIAL ® (PROPANAL, 2-METHYL-3-(4-TERT-BUTYLPHENYL)-) | 4.0000 |
| GALAXOLIDE ®, 50% in DEP (1,1,2,3,3,8-hexamethyl-1,2,3,5,7,8-hexahydro-6-oxa-cyclopenta[b]naphthalene) | 12.0000 |
| ISORALDEINE ® 70 ((E)-3-methyl-4-(2,6,6-trimethylcyclohex-2-enyl)but-3-en-2-one) | 3.0000 |
| ALLYL AMYL GLYCOLATE | 0.7000 |
| ISO E SUPER ® (BICYCLO[4.4.0]DECENE, 3-ACETYL-3,4,10,10-TETRAMETHYL-1(6)-) | 8.0000 |
| ROSE BASE | 8.0000 |
| GALBANUM BASE | 8.0000 |
| APPLE BASE | 2.5000 |
| OZONIL, 10% in DPG (DODECENYL CYANIDE, 1Z-) | 1.5000 |
| MELONAL ®, 10% in DPG (HEPTENAL, 2,6-DIMETHYL-5-) | 0.3000 |
| METHYL OCTINE CARBONATE, 10% in DPG | 0.5000 |
| DAMASCONE DELTA, 10% in DPG (1-(2,6,6-trimethylcyclohex-3-enyl)but-2-en-1-one) | 0.7000 |
| SANDRANOL ® (BUTENOL, 2-ETHYL-4-(2,2,3-TRIMETHYL-3-CYCLOPENTENYL)-2E-) | 2.0000 |
| VERTOCITRAL (CYCLOHEXENE, TRANS-2,4-DIMETHYL-1-FORMYL-3-) | 0.3000 |
| AGRUMEX (ACETIC ACID 2-TERT-BUTYLCYCLO-HEXYL ESTER) | 8.0000 |
| BENZYLACETONE | 1.0000 |
| ALDEHYDE C12 MNA (methyl nonyl acetaldehyde) | 0.5000 |
| PROJASMON P (CYCLOPENTANONE, 2-HEPTYL-) | 1.0000 |
| NEROLIN YARA YARA | 1.5000 |
| INTRELEVEN ALDEHYDE (10-undecenal), 10% in DPG | 0.5000 |
| PATCHOULI OIL | 1.5000 |
| Total | 100.0000 |

TABLE 13

Example mixture 10

| Substance | wt % |
|---|---|
| 1,4-CINEOLE | 0.3000 |
| DECALACTONE-DELTA | 0.0100 |
| DODECANLACTONE-GAMMA | 0.4000 |
| ETHANOL | 5.0000 |
| GERANIOL | 0.2000 |
| DPG | 32.2800 |
| CEDAR WOOD OIL | 0.8000 |
| AMBROCENIDE ®, 10% in DPG | 0.1000 |
| ROSEMARY OIL | 0.8000 |
| DIHYDROMYRCENOL | 8.0000 |
| ISOBUTYL QUINOLINE | 0.0500 |
| AMBROXAN | 0.1000 |
| LIGUSTRAL (CYCLOHEXENE, TRANS-2,4-DIMETHYL-1-FORMYL-3-) | 0.2000 |
| AMYL SALICYLATE N/ISO | 2.4000 |
| CITRONELLOL | 0.8000 |
| VERTOFIX (1-(3,6,8,8-tetramethyl-2,3,4,7,8,8a-hexahydro-1H-3a,7-methanoazulen-5-yl)ethanone) | 3.0000 |
| HEXYL CINNAMALDEHYDE ALPHA | 5.0000 |
| COUMARIN | 0.4000 |
| COUMARONE (BENZOFURAN, 2-ACETYL-) | 0.0600 |
| ISOBORNYL ACETATE | 3.0000 |
| CAMPHOR | 0.8000 |
| LILIAL ® (PROPANAL, 2-METHYL-3-(4-TERT-BUTYLPHENYL)-) | 3.0000 |
| LINALOOL | 4.0000 |
| LINALYL ACETATE | 4.0000 |
| TERPINEOL | 10.0000 |

TABLE 13-continued

Example mixture 10

| Substance | wt % |
|---|---|
| GALAXOLIDE ®, 50% in DEP (1,1,2,3,3,8-hexamethyl-1,2,3,5,7,8-hexahydro-6-oxacyclopenta[b]naphthalene) | 2.4000 |
| GLOBALIDE ® (PENTADECEN-1,15-OLIDE, 11E/Z) | 0.5000 |
| ETHYLENE BRASSYLATE (BRASSYLIC ACID ETHANEDIOL ESTER) | 2.4000 |
| AGRUNITRILE (HEPTENYL CYANIDE, 2,6-DIMETHYL-5-) | 1.6000 |
| ISORALDEINE ® 70 ((E)-3-methyl-4-(2,6,6-trimethylcyclohex-2-enyl)but-3-en-2-one) | 2.0000 |
| ALLYL AMYL GLYCOLATE (ACETIC ACID ALLYL ESTER, 2-METHYLBUTOXY-) | 1.5000 |
| DAMASCONE DELTA ((1-(2,6,6-trimethylcyclohex-3-enyl)but-2-en-1-one) | 0.2000 |
| TIMBEROL ® (CYCLOHEXANE, 2,2,6-TRIMETHYL-1-(3-HYDROXYHEXYL)-) | 0.2000 |
| LEMON OIL TERPENE | 2.0000 |
| CALONE ® 1951, 10% in DPG (BENZODIOXEPINONE, 7-METHYL-3,4-DIHYDRO-3-) | 0.4000 |
| EUGENOL | 0.1500 |
| FARENAL ® (UNDECENAL, 2,6,10-TRIMETHYL-9-) | 0.0500 |
| LIME OIL | 1.2000 |
| ANETHOLE | 0.4000 |
| METHYL NAPHTHYL KETONE BETA | 0.3000 |
| Total | 100.0000 |

TABLE 14

Example mixture 11

| Substance | wt % |
|---|---|
| 1,4-CINEOLE | 0.3000 |
| HEPTALACTONE-GAMMA | 0.0020 |
| OCTALACTONE-GAMMA | 0.0020 |
| NONALACTONE-GAMMA | 0.0020 |
| UNDECALACTONE-GAMMA | 0.0020 |
| DECALACTONE-DELTA | 0.0020 |
| DODECALACTONE-GAMMA | 0.4000 |
| ETHANOL | 2.0000 |
| FREESIOL | 1.5000 |
| DPG | 2.6400 |
| JASMOL | 0.5000 |
| TOCPHEROL | 0.0500 |
| CASSIS BASE | 1.0000 |
| CLOVE FLOWER OIL | 0.5000 |
| PATCHOULI OIL | 0.5000 |
| DIHYDROMYRCENOL | 6.0000 |
| HEXYL SALICYLATE | 2.0000 |
| HEDIONE ® (METHYL CIS/TRANS-DIHYDRO-JASMONATE) | 21.0000 |
| ORANGE OIL | 2.5000 |
| GLOBALIDE ® (PENTADECEN-1,15-OLIDE, 11E/Z) CYCLOPENTENYL)-4-) | 2.0000 0.5000 |
| LAVANDIN OIL GROSSO | 2.0000 |
| YSAMBER ® K (ISOLONGIFOLANONE ETHANEDIOL KETAL) | 2.0000 |
| HEXYL CINNAMALDEHYDE ALPHA | 8.0000 |
| LILIAL ® (PROPANAL, 2-METHYL-3-(4-TERT-BUTYLPHENYL)-) | 1.0000 |
| LINALOOL | 6.0000 |
| LINALYL ACETATE | 5.0000 |
| TERPINEOL | 1.8000 |
| ETHYLENE BRASSYLATE (BRASSYLIC ACID ETHANEDIOL ESTER) | 2.0000 |
| ALLYL AMYL GLYCOLATE (ACETIC ACID ALLYL ESTER, 2-METHYLBUTOXY-) | 1.0000 |
| ISO E SUPER ® (BICYCLO[4.4.0]DECENE, 3-ACETYL-3,4,10,10-TETRAMETHYL-1(6)-) | 4.5000 |
| KEPHALIS (CYCLOHEXANONE, 3,3,5,5-TETRAMETHYL-4-(1-ETHOXYVINYL)-) | 4.5000 |
| BERGAMOT BASE | 8.0000 |

TABLE 14-continued

Example mixture 11

| Substance | wt % |
|---|---|
| FLORALOZONE (PROPANAL, 2-METHYL-2-(4-ETHYLBENZYL)-) | 1.0000 |
| MANDARINE ALDEHYDE, 10% in TEC (DODECENAL, 2E-) | 0.5000 |
| LIGUSTRAL ® 10% in DPG (CYCLOHEXENE, TRANS-2,4-DIMETHYL-1-FORMYL-3-) | 0.8000 |
| DAMASCONE ALPHA, 1% in DPG ((E/Z)-1-(2,6,6-trimethylcyclohex-2-enyl)but-2-en-1-one) | 2.0000 |
| FARENAL ®, 1% in DPG (UNDECENAL, 2,6,10-TRIMETHYL-9-) | 1.5000 |
| LEAFOVERT ®, 10% in DPG (CARBONIC ACID 3Z-HEXENYLMETHYL ESTER) | 2.0000 |
| CALONE ® 1951, 10% in DPG (BENZODIOXEPINONE, 7-METHYL-3,4-DIHYDRO-3-) | 3.0000 |
| Total | 100.0000 |

TABLE 15

Example mixture 12

| Substance | wt % |
|---|---|
| 1,4-CINEOLE | 0.3000 |
| HEPTALACTONE-GAMMA | 0.0020 |
| OCTALACTONE-GAMMA | 0.0020 |
| NONALACTONE-GAMMA | 0.0020 |
| UNDECALACTONE-GAMMA | 0.0020 |
| DECALACTONE-DELTA | 0.0020 |
| DODECALACTONE-GAMMA | 0.4000 |
| ETHANOL | 2.0000 |
| FREESIOL | 1.5000 |
| DPG | 1.7400 |
| TOCOPHEROL | 0.0500 |
| CLOVE FLOWER OIL | 1.0000 |
| PATCHOULI OIL | 5.0000 |
| DIHYDROMYRCENOL | 6.0000 |
| ISORALDEINE ® ((E)-3-methyl-4-(2,6,6-trimethylcyclohex-2-enyl)but-3-en-2-one) | 2.0000 |
| EBANOL (PENTEN-2-ONE, 3-METHYL-5-(2,2,3-TRIMETHYL-3-CYCLOPENTENYL)-4E/Z-) | 1.5000 |
| GLOBALIDE ® (PENTADECEN-1,15-OLIDE, 11E/Z) | 6.0000 |
| HEXYL CINNAMALDEHYDE ALPHA | 4.0000 |
| COUMARIN | 2.0000 |
| LILIAL ® (PROPANAL, 2-METHYL-3-(4-TERT-BUTYLPHENYL)-) | 3.0000 |
| LINALOOL | 2.0000 |
| LINALYL ACETATE | 3.0000 |
| VANILLIN | 2.0000 |
| LYRAL ® (CYCLOHEXENE, 4-FORMYL-2-(4-HYDROXY-4-METHYLPENTYL)-) | 4.0000 |
| HEDIONE ® (METHYL CIS/TRANS-DIHYDRO-JASMONATE) | 3.0000 |
| EVERNYL ® (BENZOIC ACID METHYL ESTER, 2,4-DIHYDROXY-3,6-DIMETHYL-) | 0.5000 |
| CEDRAMBER (CEDRYL METHYL ETHER) | 2.0000 |
| ISO E SUPER ® (BICYCLO[4.4.0]DECENE, 3-ACETYL-3,4,10,10-TETRAMETHYL-1(6)-) | 15.0000 |
| *GERANIUM* BASE | 2.0000 |
| BERGAMOT BASE | 7.0000 |
| MUGWORT OIL | 1.0000 |
| GALBANUM OIL, 10% in DPG | 1.5000 |
| AMBROCENIDE ®, 0.1% in DPG | 2.0000 |
| CYCLOGALBANATE ®, 10% in DPG (CYCLOHEXYLOXYACETIC ACID ALLYL ESTER) | 0.5000 |
| *CISTUS* OIL, 10% in DPG | 1.0000 |
| SPEARMINT OIL (SPEARMINT), 10% in DPG | 1.0000 |
| AURELIONE (CYCLOHEXADECENONE, 7/8E/Z-) | 12.0000 |
| AMBROXIDE | 0.5000 |
| MANDARIN OIL | 0.5000 |
| LAVANDIN OIL GROSSO | 3.0000 |
| Total | 100.0000 |

TABLE 16

Example mixture 13

| Substance | wt % |
|---|---|
| DECALACTONE-DELTA | 0.0020 |
| DODECALACTONE-GAMMA | 0.4000 |
| ETHANOL | 2.0000 |
| GERANIOL | 1.5000 |
| DPG | 2.8480 |
| TOCOPHEROL | 0.0500 |
| AGRUMEX LC | 0.5000 |
| ALDEHYDE C14 SO-CALLED | 0.2000 |
| AMAROCIT ® | 0.2000 |
| AMBERWOOD ® F | 1.0000 |
| BENZOIN SIAM RESIN, 50% IN BB | 0.3000 |
| BERGAMOT SYNTHESSENCE AFRICAN | 4.0000 |
| CEDAR WOOD OIL VIRGINIA | 3.0000 |
| CEDRAMBER | 1.5000 |
| COUMARIN | 0.3000 |
| DIETHYL MALONATE | 0.8000 |
| DIHYDROMYRCENOL | 0.8000 |
| ETHYL DECADIENOATE TRANS CIS-2,4, 10% in IPM | 1.0000 |
| ETHYLVANILLIN | 0.4000 |
| ETHYLENE BRASSYLATE | 12.0000 |
| FLOROSA | 3.0000 |
| GERANYL ACETATE | 0.5000 |
| GINGER OIL CHINESE | 0.2000 |
| GIVESCONE, 10% in DPG | 0.6000 |
| HEDIONE | 6.5000 |
| HELIONAL | 3.0000 |
| HEXENYL ACETATE CIS-3, 10% in DPG | 2.0000 |
| HEXYL SALICYLATE | 6.5000 |
| INDOLE, 10% in DPG | 0.3000 |
| ISO E SUPER | 22.5000 |
| LINALOOL | 3.0000 |
| LINALYL ACETATE | 4.0000 |
| METHYL ANTHRANILATE | 0.2000 |
| METHYL NAPHTHYL KETONE BETA CRIST. | 0.3000 |
| NEROLIDOL | 0.5000 |
| ORANGE OIL BRAZILIAN | 6.0000 |
| PRENYL ACETATE, 10% in DPG | 1.0000 |
| SANDRANOL ® | 1.0000 |
| STYRALLYL ACETATE, 10% in DPG | 0.8000 |
| SYMROXANE ® | 0.3000 |
| TETRAHYDROLINALOOL | 5.0000 |
| Total | 100.0000 |

The present invention is described in more detail below on the basis of selected, specific examples of use. As already pointed out, these examples serve only to illustrate the invention without limiting said invention or restricting said invention thereto.

Liquid Soap

TABLE 17

Liquid soap

| | Constituent | INCI | wt % |
|---|---|---|---|
| Phase A | Water | Water | 77.4360 |
| | Plantacare PS 10 | Sodium laureth sulfate, lauryl glucoside | 20.0000 |

TABLE 17-continued

| | Liquid soap | | |
|---|---|---|---|
| | Constituent | INCI | wt % |
| | Preservative | | 0.5000 |
| | Sodium chloride | Sodium chloride | 1.4000 |
| | Citric acid monohydrate | Citric acid | 0.1640 |
| Phase B | DPG | Dipropylene glycol | 0.4253 |
| | gamma-Dodecalactone | | 0.0122 |
| | gamma-Decalactone | | 0.0090 |
| | Ethanol | | 0.0500 |
| | Geraniol | | 0.0025 |
| | Linalool | | 0.0010 |
| | Total | | 100.0000 |

Phase A is produced by putting together all the listed constituents in succession in accordance with the order of this list at room temperature and under stirring. Phase B, which corresponds to inventive substance mixture 1, is premixed and is added to completed phase A. If necessary, the pH can be adjusted to 6.0 with citric acid or sodium hydroxide.

Shampoo

TABLE 18

| Shampoo | | |
|---|---|---|
| Constituent | INCI | wt % |
| Water | Water | 71.3000 |
| Citric acid monohydrate | Citric acid | 0.1000 |
| Euperlan PK 771 | Glycol distearate, sodium laureth sulfate, cocamide MEA, laureth-10 | 6.0000 |
| Sodium chloride | Sodium chloride | 1.4000 |
| Plantacare PS 10 | Sodium laureth sulfate, lauryl glucoside | 20.0000 |
| Preservative | | 0.5000 |
| Example mixture 4 | Perfume | 0.7000 |
| Total | | 100.0000 |

Production is carried out by putting together all the listed constituents in succession in accordance with the order of this list at room temperature and under stirring. If necessary, the pH can be adjusted to 6.0 with citric acid or sodium hydroxide.

Laundry Soap

TABLE 19

| Laundry soap | | |
|---|---|---|
| Constituent | INCI | wt % |
| Britesil H 20 | Sodium silicate | 14.6500 |
| Dolomite | Sudesan | 25.0000 |
| Base soap HTS | Sodium tallowate, sodium cocoate, sodium palm kernelate | 45.0000 |
| Marlon ARL | C-10-13, ABS-Na, powder | 6.7000 |
| Texapon Z HK powder | Sodium fatty alcohol C12-C18 | 6.6000 |
| Titanium dioxide | Titanium dioxide | 1.0000 |
| Color Acid Blue 7, C.I. 42080 powder | | 0.2000 |
| Example mixture 4 | Perfume | 0.8500 |
| Total | | 100.0000 |

The constituents are mixed in a kneader and shaped into a soap bar using an extruder.

Makeup Remover

Production is carried out in a Becomix.

To produce phase A, the glycerol and the Surfhope® C1216 is added to the Becomix and stirred at 0.3 m/s at −0.5 bar, followed by homogenization using a Turrax at 3 m/s for 4 minutes. After complete dissolution of the Surfhope® C1216, the Surfhope® C1616 is added, with continuation of stirring at 0.3 m/s.

The subsequent homogenization is done using a Turrax at 3 m/s for 4 minutes. Thereafter, the water is added and homogenization is carried out again using a Turrax at 3 m/s for 6 minutes.

This mixture is heated to 80° C. under stirring at 0.3 m/s, then brought to 50° C., and homogenized again using a Turrax at 3 m/s for 2 minutes. Thereafter, the temperature is increased to 80° C. and a pressure of −0.6 bar is set.

TABLE 20

| Makeup remover | | |
|---|---|---|
| Constituent | INCI | wt % |
| Phase A | | |
| Glycerol | Glycerol | 10.0000 |
| Surfhope ® C-1216 | Sucrose laurate | 3.0000 |
| Surfhope ® C-1616 | Sucrose palmitate | 3.0000 |
| Water | Water (aqua) | 5.0000 |
| Phase B | | |
| Neutral oil | Caprylic/capric triglyceride | 47.7100 |
| Dragoxat ® 89 | Ethylhexyl isononanoate | 30.0000 |
| Ionol CP | BHT | 0.0500 |
| Phase C | | |
| Symdiol ® 68 | 1,2-Hexanediol, caprylyl glycol | 0.8000 |
| Phase D | | |
| Example mixture 2 | Perfume | 0.1500 |
| Color I | Color | 0.1500 |
| Color II | Color | 0.1400 |
| Total | | 100.0000 |

Phase B is produced at 80° C. At a temperature of 80° C., the constituents of phase B are mixed very slowly in succession and very slowly and then stirred at 0.5 m/s and also homogenized using a Turrax at 3 m/s for 2 minutes. After addition of a quarter of the oil to the tank, a homogenization step is carried out using a Turrax at 5 m/s for 4 minutes.

After addition of half of the amount of oil, homogenization is carried out again using a Turrax at 5 m/s for 4 minutes and the stirring speed is increased to 0.8 m/s.

After addition of three quarters of the oil, there follows a homogenization step using a Turrax at 5 m/s for 4 minutes and an increase in the stirring speed to 1 m/s. Then, the remaining amount of the oil is added and stirred at 1.2 m/s.

After addition of phase C, the pressure is increased to −0.8 bar and homogenization is carried out using a Turrax at 5 m/s for 4 minutes.

The preparation is cooled to 25° C. under stirring at 0.5 m/s, the stirring speed being reduced in this process. Then, phase D is added at 40° C.

Color I: 0.1% solution in isopropyl palmitate of D&C Red No. 17 C.I. 26100

Color II: 0.1% solution in isopropyl palmitate of Phat Brown DC 8206: C.I. 47000, C.I. 26100, C.I. 60725

The final preparation has a viscosity of 69 280 cP.

Dishwashing Liquid

TABLE 21

| Constituent | INCI | wt % |
| --- | --- | --- |
| *Dishwashing liquid* | | |
| Water, demineralized | Water | 41.8000 |
| Glucopon 650 EC | Coco-glucoside | 4.0000 |
| Zetesol NL-2 | Sodium laureth sulfate | 45.0000 |
| Dehyton AB 30 | Coco-betaine | 8.0000 |
| Ethanol 96% | Ethanol | 1.0000 |
| Parmatol MBX | Benisothiazolinone, methylisothiazolinone, laurylamine, dipropylenediamine | 0.1000 |
| Example mixture 4 | Perfume | 0.1000 |
| Total | | 100.0000 |

Production is carried out by adding all the constituents in the order of the list, with attention being paid to completely dissolving each constituent before adding the next constituent. The pH is adjusted to pH=7 using citric acid.

Hair Conditioner

TABLE 22

| Constituent | INCI | wt % |
| --- | --- | --- |
| *Hair conditioner* | | |
| *Phase A* | | |
| Hostaphat Kw 340 D | Trieteareth-4 phospate | 10.0000 |
| Medium mineral oil | Paraffinum liquidum | 6.0000 |
| Lunacera M | Ozocerite | 5.0000 |
| Isopropyl myristate | Isopropyl myristate | 5.0000 |
| Xiameter ® PMX-200 silicone fluid | Dimethicone | 0.5000 |
| Lanolin alcohol | Lanolin alcohol | 0.5000 |
| *Phase B* | | |
| Water | Water (aqua) | 29.1000 |
| Preservative | | 0.8000 |
| Glycerol, 99.5 P. | Glycerol | 12.0000 |
| Citric acid, 20% aqueous solution | Citric acid | 1.3000 |
| *Phase C* | | |
| Water | Water (aqua) | 28.9000 |
| Carbopol ® Ultrez-10 | Caromer | 0.2000 |
| Triethanolamine, 99% | Triethanolamine | 0.3000 |
| *Phase D* | | |
| Example mixture 5 | Perfume | 0.4000 |
| Total | | 100.0000 |

To produce the hair conditioner, all the constituents of phase A are mixed and are heated to 75° C.

To produce phase B, first the water is heated to 80° C. and then the remaining constituents of phase B are admixed and homogenized. Then, phase A is added to phase B under stirring.

To produce phase C, the Ultrez-10 is left to swell in the water under strong stirring, then the triethanolamine is added to obtain a clear gel preparation, which is then heated to 45° C. The mixture of phase A and B are added to the phase C heated to 45° C., and homogenized at room temperature.

Then, phase D, example mixture 5, is added.

If necessary, the pH should be adjusted to pH=4 using citric acid or sodium hydroxide.

Heavy-Duty Liquid Laundry Detergent

TABLE 23

| Constituent | INCI | wt % |
| --- | --- | --- |
| *Heavy-duty liquid laundry detergent* | | |
| 1 Water, demineralized | Water | 39.7000 |
| 2 Tinopal CBS-X | Disodium distyrylbiphenyl disulfonate | 0.1000 |
| 3 Edenor K 12-18 | Cocos fatty acids | 7.5000 |
| 4 Potassium hydroxide, 50% solution | Potassium hydroxide | 4.3000 |
| 5 Propylene glycol 1,2 | Propane-1,2-diol | 5.0000 |
| 6 Hoesch T 9, 90% | Trideceth-9 | 12.0000 |
| 7 Parmatol A 26 | Mixture of 5-chloro-2-methyl-2H-isothiazol-3-one and 2-methyl-2H-isothiazol-3-one | 0.2000 |
| 8 Hoesch NAS 60 | Sulfonic acid, C 13-17-sec-alkyl-, sodium salt | 17.0000 |
| 9 Triethanolamine pure C | Triethanolamine | 2.0000 |
| 10 Trisodium citrate dihydrate | Trisodium citrate dihydrate | 5.0000 |
| 11 Hoesch Phos DET 32 D | Diethylenetriamine pentamethylene phosphonic acid sodium salt | 3.0000 |
| 12 Ethanol 96% | Ethanol | 3.0000 |
| 13 Alcalase 2.5 L | Protease | 0.4000 |
| 14 Termamyl 300L | alpha-Amylase | 0.3000 |
| 15 Example mixture 5 | Perfume | 0.5000 |
| Total | | 100.0000 |

Production is carried out by mixing constituents 1 and 2 and by heating to 50° C. Then, constituents 3 and 4 are added and stirred until soap has formed. After addition of constituents 5 to 10 in the order of the list and cooling to 30° C., constituents 11 to 14 are added in the order of the list. If necessary, the pH is adjusted to 8.5.

Liquid Laundry Detergent

Production is carried out by initially charging the water in a vessel and by heating to 70° C. under stirring. Then, constituents 2 and 3 are added in this order and stirred without further heating for 30 minutes. Then, all the constituents are added in the order of the list, with attention being paid to completely dissolving each constituent before adding the next constituent. The pH is adjusted to pH=9 using citric acid.

TABLE 24

| Constituent | INCI | wt % |
| --- | --- | --- |
| *Liquid laundry detergent* | | |
| 1 Water, demineralized | Water | 48.3000 |
| 2 Edenor K 12-18 | Cocos fatty acids | 3.0000 |
| 3 Sodium hydroxide, 50% solution | Sodium hydroxide | 2.5000 |
| 4 Novethix L-10 polymer | NRC Nordmann, Rassmann | 2.5000 |
| 5 Zetesol NL-2 | Sodium laureth sulfate | 30.0000 |

TABLE 24-continued

Liquid laundry detergent

| Constituent | INCI | wt % |
|---|---|---|
| 6 Hoesch AE 50 | Sodium dodecylbenzenesulfonate | 3.0000 |
| 7 Dehydol LT 7 | | 3.0000 |
| 8 Hoesch Phos DET 32 D | Diethylenetriamine pentamethylene phosphonic acid sodium salt | 1.0000 |
| 9 Ethanol, 96% | Ethanol | 2.0000 |
| 10 Propylene glycol 1,2 | Propane-1,2-diol | 2.0000 |
| 11 Trisodium citrate dihydrate | Trisodium citrate dihydrate | 2.0000 |
| 12 Example mixture 5 | Perfume | 0.5000 |
| 13 Parmatol A 26 | Mixture of 5-chloro-2-methyl-2H-isothiazol-3-one and 2-methyl-2H-isothiazol-3-one | 0.2000 |
| | Total | 100.0000 |

Fabric Softener

TABLE 25

Fabric softener

| Constituent | INCI | wt % |
|---|---|---|
| 1 Water, demineralized | Water | 93.1000 |
| 2 Parmetol K 40 | N,S-Heterocycles | 0.1000 |
| 3 Xiameter AFE-1520 | Simethicone | 0.3000 |
| 4 Rewoquat WE 18 | Di(tallow carboxyethyl) hydroxyethyl methylammonium methosulfate | 5.5000 |
| 5 Example mixture 5 | Perfume | 1.0000 |
| | Total | 100.0000 |

Production is carried out by initially charging the water in a vessel and by heating to 45° C. Then, constituent 2 is added under strong stirring and is heated continuously up to 50° C. until constituent 2 is completely dissolved. Then, constituents 3 and 4 are added separately in succession in the order of the list. After cooling to 25° C., constituent 5 is added and is then strongly stirred for 30 minutes. Lastly, the pH is adjusted to pH=3 using citric acid or sodium hydroxide.

Lip Care Stick

Production is carried out by melting all the constituents in the order of the list without the perfume and by homogenizing while heating to 70° C. At a temperature of 50° C., the perfume is added and homogenized.

TABLE 26

Lip care stick

| Constituent | INCI | wt % |
|---|---|---|
| Cetiol 868 | Ethylhexyl stearate | 5.0000 |
| Cutina ® FS 45 | Stearic acid, palmitic acid | 1.5000 |
| Elfacos E 200 | Methoxy PEG-22 and dodecyl glycol copolymer | 4.0000 |
| Ivarlan 3360 | Glyceryl lanolate | 3.0000 |
| Jojoba oil | | 1.0000 |
| Medium mineral oil | Paraffinum liquidum | 25.9950 |
| Neutral oil | Caprylic/capric triglyceride | 10.0000 |
| Paraffin 52-54 | Paraffin | 12.0000 |
| Permulgin 3220 | Ozokerite | 20.0000 |

TABLE 26-continued

Lip care stick

| Constituent | INCI | wt % |
|---|---|---|
| Permulgin 3430 | Copernicia cerifera (carnauba) wax | 2.0000 |
| Prisorine Sqs 3758 | Hydrogenated polyisobutene | 5.0000 |
| Softisan 100 | Hydrogenated cocoglycerides | 5.0000 |
| Super Hartolan | Lanolin alcohol | 1.4000 |
| Titanium dioxide | Titanium dioxide | 0.1000 |
| Xiameter ® PMX-0245 cyclosiloxane | Cyclopentasiloxane | 4.0000 |
| Example mixture 3 | Perfume | 0.0050 |
| | Total | 100.000 |

Night Cream

TABLE 27

Night cream

| Constituent | INCI | wt % |
|---|---|---|
| Phase A | | |
| Dragosan W/O P | Sorbitan isostearate, hydrogenated castor oil, beeswax (cera alba) | 5.0000 |
| Dragoxat ® 89 | Ethylhexyl isononanoate | 5.0000 |
| Medium mineral oil | Paraffinum liquidum | 15.1000 |
| Tece Ozokerit N 325/II | Ozokerite | 2.3000 |
| Vaseline | Petrolatum | 4.5000 |
| Phase B | | |
| Water | Water (aqua) | 64.0970 |
| Glycerol, 99.5 P. | Glycerol | 3.0000 |
| Magnesium sulfate heptahydrate | Magnesium sulfate | 0.7000 |
| Preservative complex (ND liquid) | Triethylene glycol, imidazolidinyl urea, methylparaben | 0.3000 |
| Phase C | | |
| Example mixture 2 | Perfume | 0.0030 |
| | Total | 100.0000 |

Production is carried out by heating each of phase A and B individually to approx. 80° C. Then, phase B is added to phase A using an Ultra-Turrax and emulsified. While stirring with a paddle stirrer, this mixture is cooled and is then emulsified again at approx. 60° C. When the mixture has reached a temperature of approx. 35° C., phase C is added.

Body Lotion

TABLE 28

Body lotion

| Constituent | INCI | wt % |
|---|---|---|
| Phase A | | |
| Covabsorb | Ethylhexyl methoxycinnamate, butyl | 0.4000 |
| Dragoxat ® 89 | Ethylhexyl isononanoate | 3.7500 |
| Emulium 22 | Tribehenin PEG-20 ester | 4.0000 |
| Lantte ® O | Cetearyl alcohol | 1.0000 |
| PCL liquid | Cetearyl ethylhexanoate, isopropyl myristate | 2.2500 |
| Xiameter ® PMX-0245 cyclosiloxane | Cyclopentasiloxane | 3.7500 |

TABLE 28-continued

Body lotion

| Constituent | INCI | wt % |
|---|---|---|
| | Phase B | |
| Water | Water | 78.8500 |
| Sodium benzoate | Sodium benzoate | 0.1000 |
| | Phase C | |
| Glycerol, 99.5 P. | Perfume | 5.0000 |
| Preservative complex (ND liquid) | Triethylene glycol, imidazolidinyl urea, methylparaben | 0.9000 |
| | Phase D | |
| Sodium hydroxide, 30% solution | Sodium hydroxide | 0.1300 |
| | Phase E | |
| Example mixture 2 | Perfume | 0.0100 |
| | Total | 100.0000 |

To produce phase B, the sodium benzoate is added to the water and is mixed until it is completely dissolved. Then, the premixed phase C is added to phase B and is heated to 75° C. while stirring using a magnetic stirrer.

The constituents of phase A are mixed separately and are then heated and homogenized in a water bath. While stirring (Rayneri=deflocculator or at least one helix), phase A is added to the mixture of phase B and C. Thereafter, this mixture is cooled to 30° C. while stirring (helix).

Subsequently, phase D is added to adjust the pH to 6.0. Thereafter, phase E, the perfume, is added.

Laundry Powder

TABLE 29

Laundry powder

| Constituent | INCI | wt % |
|---|---|---|
| Sodium metasilicate pentahydrate | Sodium metasilicate pentahydrate | 48.0000 |
| Natrium hydrogen carbonate | Sodium hydrogen carbonate | 15.0000 |
| Sodium percarbonate | Sodium carbonate peroxyhydrate | 15.0000 |
| Peractive AC Blue | TAED/Na carboxymethylcellulose | 5.0000 |
| Genapol AO-080 | Oxo alcohol C14-15, 8EO | 3.0000 |
| Texapon K12 powder | Sodium lauryl sulfate C12 | 7.0000 |
| Tinopal CBS-X | | 0.5000 |
| Savinase 6.0 T, type W | Protease | 0.4000 |
| Termamyl 120 T | alpha-Amylase | 0.3000 |
| Sodium sulfate | Sodium sulfate | 5.5000 |
| Example mixture 9 | Perfume | 0.3000 |
| | Total | 100.0000 |

All-Purpose Cleaner

TABLE 30

All-purpose cleaner

| Constituent | INCI | wt % |
|---|---|---|
| Deionized water | Water | 59.6000 |
| Mergal K9N | 5-Chloro-2-methyl-3-(2H)-isothiazolone and 2-methyl-3-(2H)-isothiazolone | 0.1000 |
| Trisodium citrate dihydrate | Trisodium citrate dihydrate | 3.0000 |
| Zetesol NL-2 | Fatty alcohol C12-14-sulfate, sodium | 30.0000 |
| Imbentin C/125/055 | Fatty alcohol C12-15, 8EO | 5.0000 |
| Ethanol, 96% | Ethanol | 2.0000 |
| Example mixture 10 | Perfume | 0.3000 |
| | Total | 100.0000 |

Shampoo

TABLE 31

Shampoo

| Constituent | INCI | wt % |
|---|---|---|
| Deionized water | Water | 71.5000 |
| Plantacare PS 10 | Sodium laureth sulfate, lauryl glucoside | 20.0000 |
| Euperlan PK 771 | Glycol distearate, sodium lauryl sulfate, cocamide | 6.0000 |
| Dragocide liquid | Phenoxyethanol, methylparaben, ethylparaben | 0.5000 |
| Sodium chloride | Sodium chloride | 1.4000 |
| Citric acid monohydrate, crystalline | Citric acid | 0.1000 |
| Example mixture 12 | Perfume | 0.5000 |
| | Total | 100.0000 |

Shower Gel

TABLE 32

Shower gel

| Constituent | INCI | wt % |
|---|---|---|
| Deionized water | Water | 76.3000 |
| Plantacare PS 10 | Sodium laureth sulfate, lauryl glucoside | 20.0000 |
| Dragocide liquid | Phenoxyethanol, methylparaben, ethylparaben | 0.5000 |
| Sodium chloride | Sodium chloride | 1.4000 |
| Citric acid monohydrate, crystalline | Citric acid | 1.3000 |
| Example mixture 11 | Perfume | 0.5000 |
| | Total | 100.0000 |

Transparent Deodorant Stick (Formulation A) and Cream Deodorant Cream Stick (Formulation B)

TABLE 33

Transparent deodorant sticks

| Constituent | A wt % | B wt % |
|---|---|---|
| Deionized water | 36.5500 | 54.8500 |
| Aluminum zirconium tetrachlorohydrate - glycine complex | 25.0000 | 25.0000 |
| Dimethicone (10 Cst) | — | 5.0000 |

TABLE 33-continued

Transparent deodorant sticks

| Constituent | A wt % | B wt % |
|---|---|---|
| Cyclopentasiloxane | — | 1.0000 |
| Petrolatum | 5.0000 | 5.0000 |
| Ozokerite | 1.0000 | — |
| Stearyl alcohol | 12.0000 | — |
| 2-Butyloctanoic acid | 0.5000 | 0.5000 |
| Wax | — | 1.2500 |
| PPG-14 butyl ether | 9.0000 | — |
| Hardened rapeseed oil | — | 5.0000 |
| Silicon dioxide | — | 1.0000 |
| Farnesol | 0.2500 | 0.2500 |
| Paraffin oil | 0.5000 | — |
| Hydrogenated castor oil (castor wax) | 3.5000 | — |
| Talc | 4.0000 | — |
| Behenyl alcohol | 0.2000 | — |
| D-Panthenyl triacetate | 1.0000 | — |
| Example mixture 13 | 1.5000 | 1.1500 |
| Total | 100.0000 | 100.0000 |

Roll-on Antiperspirant

TABLE 34

Roll-on antiperspirant

| Constituent | wt % |
|---|---|
| Deionized water | 72.9000 |
| Caprylyl trimethicone (SilCare TM Silicone 31 M 50) | 0.3000 |
| Steareth-20 (GENAPOL TM HS 200) | 3.0000 |
| Steareth-2 (GENAPOL TM HS 020) | 1.5000 |
| Dicaprylyl ether (Cetiol TM OE) | 2.0000 |
| Coco caprylate/caprate (Cetiol TM LC) | 2.0000 |
| Glycerol | 2.0000 |
| Glyceryl stearate (Cutina TM GMS) | 2.0000 |
| Octyldodecanol (Eutanol TM G) | 1.0000 |
| Stearyl alcohol | 2.5000 |
| Aluminum chlorohydrate as per Example 1 of EP 1321431 | 10.0000 |
| Avocado extract, Persea gratissima | 0.3000 |
| Example mixture 12 | 0.5000 |
| Total | 100.0000 |

Aerosol Spray

TABLE 35

Aerosol spray

| Constituent | wt % |
|---|---|
| Ethanol | 96.2000 |
| Octyldodecanol | 0.5000 |
| 1,2-Pentanediol | 1.0000 |
| 1,2-Hexanediol | 0.2500 |
| 1,2-Octanediol | 0.2500 |
| Farnesol | 0.5000 |
| Ethylhexylglycerin (octoxyglycerin) | 0.5000 |
| Example mixture 5 | 0.4000 |
| Example mixture 11 | 0.4000 |
| Total | 100.0000 |

Hair Conditioner with UV Protection

TABLE 36

Hair conditioner with UV protection

| Constituent | INCI | wt % |
|---|---|---|
| Deionized water | Water | 83.2000 |
| Benzophenone-4 | Benzophenone-4 | 0.5000 |
| Dow Corning 5200 | Laurylmethicone copolyol | 0.5000 |
| Dow Corning 949 cationic emulsion | Amodimethicone, cetrimonium chloride, trideceth- | 2.0000 |
| Dragocide liquid | Phenoxyethanol (and) methylparaben (and) | 0.8000 |
| Dragoxat 89 | Ethylhexyl isononanoate | 4.0000 |
| Edeta BD | Disodium EDTA | 0.0500 |
| Emulsiphos | Potassium cetyl phosphate, hydrogenated palm | 0.5000 |
| L-Arginine | Arginine | 1.2000 |
| Lanette O | Cetearyl alcohol | 4.0000 |
| Natrosol 250 HR | Hydroxyethylcellulose | 0.2500 |
| Neo Heliopan AP | Disodium phenyl dibenzimidazole tetrasulfonate | 0.5000 |
| Neo Heliopan Hydro | Phenylbenzimidazole sulfonic acid | 2.0000 |
| Example mixture 5 | Perfume | 0.2500 |
| Example mixture 12 | Perfume | 0.2500 |
| Total | | 100.0000 |

Sunscreen Spray

TABLE 37

Sunscreen spray

| Constituent | INCI | wt % |
|---|---|---|
| Phase A | | |
| Water, demineralized | Water (aqua) | 68.9000 |
| Glycerol | Glycerol | 4.0000 |
| 1,3-Butylene glycol | Butylene glycol | 5.0000 |
| D-Panthenol | Panthenol | 0.5000 |
| Lara Care A-200 | Galactoarabinan | 0.2500 |
| Phase B | | |
| Baysilone oil M 10 | Dimethicone | 1.0000 |
| Edeta BD | Disodium EDTA | 0.1000 |
| Copherol 1250 | Tocopheryl acetate | 0.5000 |
| Cetiol OE | Dicaprylyl ether | 3.0000 |
| Neo Heliopan ® HMS | Homosalate | 5.0000 |
| Neo Heliopan ® AV | Ethylhexyl methoxycinnamate | 6.0000 |
| Neo Heliopan ® 357 | Butyl methoxydibenzoylmethane | 1.0000 |
| Corapan TQ | Diethylhexylnaphthalate | 2.0000 |
| alpha-Bisabolol | Bisabolol | 0.1000 |
| Pemulen TR-2 | Acrylates/C10-30 alkyl acrylate crosspolymer | 0.2500 |
| Phase C | | |
| Phenoxyethanol | Phenoxyethanol | 0.7000 |
| Solbrol M | Methylparaben | 0.2000 |
| Solbrol P | Propylparaben | 0.1000 |
| Phase D | | |
| NaOH, 10% | Sodium hydroxide | 0.6000 |
| | | 0.5000 |
| Phase E | | |
| Example mixture 13 | Perfume | 0.2000 |
| Example mixture 5 | Perfume | 0.1000 |
| Total | | 100.0000 |

First, the Lara Care A-200 was dissolved in the other constituents of phase A under stirring.

Then, all the raw materials of phase B were weighed out without Pemulen and the crystalline substances were dissolved under heating. After dissolution, the Pemulen was dispersed in. Thereafter, the mixture of phase B was added to to the mixture of phase A and homogenized for 1 minute. Lastly, the premixed phases C-E were added and homogenization was carried out again using the Ultra Turrax for 1-2 minutes.

Sun Cream with Sun Protection Factor 40

TABLE 38

Sun cream with sun protection factor 40

| Constituent | INCI | wt % |
|---|---|---|
| Phase A | | |
| Dehymuls PGPH | Ethylhexyl methoxycinnamate, butyl | 5.0000 |
| Copherol 1250 | Ethylhexyl isononanoate | 0.5000 |
| Permulgin 3220 | Tribehenin PEG-20 ester | 0.5000 |
| Zinc stearate | Cetearyl alcohol | 0.5000 |
| Tegosoft TN | Cetearyl ethylhexanoate, isopropyl myristate | 10.0000 |
| Neo Heliopan ® E1000 | | 2.0000 |
| Neo Heliopan ® 303 | | 5.0000 |
| Neo Heliopan ® MBC | | 3.0000 |
| Zinc oxide neutral | Cyclopentasiloxane | 5.0000 |
| Phase B | | |
| Water | Water | 62.6000 |
| Glycerol | Glycerol | 0.1000 |
| Phenoxyethanol | Phenoxyethanol | 4.0000 |
| Solbrol M | Methylparaben | 0.7000 |
| Solbrol P | Propylparaben | 0.2000 |
| Magnesium sulfate | Magnesium sulfate | 0.1000 |
| | | 0.5000 |
| Phase C | | |
| Example mixture 13 | Perfume | 0.2000 |
| Example mixture 4 | Perfume | 0.1000 |
| Total | | 100.0000 |

All the constituents of phase A were mixed and heated to approx. 85° C. Then, the constituents of phase B were mixed together, with the exception of the zinc oxide, which is dispersed in using the Ultra Turrax. The mixture of the constituents of phase B was heated to approx. 85° C. Thereafter, the mixture of phase B was added to the mixture of phase A and cooled with stirring. Subsequently, phase C was added and homogenized.

Sunscreen Milk

TABLE 39

Sunscreen milk

| Constituent | INCI | wt % |
|---|---|---|
| Phase A | | |
| Dehymuls PGPH | Polyglyeery1-2 dipolyhydroxystearate | 3.0000 |
| Beeswax 8100 | Beeswax | 1.0000 |
| Monomuls 90-0-18 | Glyceryl oleate | 1.0000 |
| Zinc stearate | Zinc stearate | 1.0000 |
| Cetiol SN | Cetearyl isononanoate | 5.0000 |
| Cetiol OE | Dicaprylyl ether | 5.0000 |
| Tegosoft TN | C12-15 alkyl benzoate | 4.0000 |
| Vitamin E | Tocopherol | 0.5000 |
| Solbrol P | Propylparaben | 0.1000 |
| Neo Heliopan ® OS | Ethylhexyl salicylate | 5.0000 |
| Neo Heliopan ® AV | Ethylhexyl methoxycinnamate | 7.5000 |
| Uvinulâ T150 | Ethylhexyl triazone | 1.5000 |
| Phase B | | |
| Water | Water | 43.5500 |
| Trilon BD | Disodium EDTA | 0.1000 |
| Glycerol | Glycerol | 5.0000 |
| Solbrol M | Methylparaben | 0.2000 |
| Phenoxyethanol | Phenoxyethanol | 0.7000 |
| Neo Heliopan ® AP, 10% solution | Disodium phenyl dibenzimidazole tetrasulfonate | 15.0000 0.5000 |
| Phase C | | |
| alpha-Bisabolol | Bisabolol | 0.1000 |
| Example mixture 12 | Perfume | 0.2500 |
| Total | | 100.0000 |

Transparent Gel Toothpaste

TABLE 40

Transparent gel toothpaste

| Constituent | wt % |
|---|---|
| Sorbitol, 70% | 63.1750 |
| Deionized water | 11.3100 |
| Sodium carboxymethylcellulose | 0.6000 |
| Sodium lauryl sulfate | 1.5000 |
| Sodium monofluorophosphate | 1.1400 |
| PEG 1500 (PEG 32) | 5.0000 |
| Pellitorin solution (containing 10% pellitorin) | 0.0250 |
| Sucrose | 0.2000 |
| Sident 22 S (thickening silica) | 8.0000 |
| Sident 9 (abrasive silica) | 8.0000 |
| Solbrol | 0.1500 |
| Trisodium phosphate | 0.1000 |
| Example mixture 7 | 0.8000 |
| Total | 100.0000 |

Phosphate-Based Toothpaste

TABLE 41

Phosphate-based toothpaste

| Constituent | wt % |
|---|---|
| Deionized water | 36.3900 |
| Aerosil ® 200 (silica) | 3.0000 |
| Dicalcium phosphate dihydrate | 36.0000 |
| Glycerol | 20.0000 |
| Sodium carboxymethylcellulose | 1.2000 |
| Sodium lauryl sulfate (Texapon) | 1.3000 |
| Sodium monofluorophosphate | 0.7600 |
| Sucrose | 0.2000 |
| Solbrol M (sodium salt) | 0.1500 |
| Example mixture 7 | 1.0000 |
| Total | 100.0000 |

Zinc-Containing Toothpaste

TABLE 42

Zinc-containing toothpaste

| Constituent | wt % |
| --- | --- |
| Deionized water | 21.2000 |
| 1,2-Propylene glycol | 5.0000 |
| Abrasive silica | 20.0000 |
| Dye (1% in water) | 0.5000 |
| Glycerol | 5.0000 |
| Na gluconate | 1.5000 |
| Na sucrose | 0.5000 |
| Sodium fluoride NaF | 0.5000 |
| Sodium hydroxide | 0.1000 |
| Sodium lauryl sulfate | 2.0000 |
| Polyethylene glycol | 1.0000 |
| Sorbitol, 70% in water | 36.0000 |
| Tetrasodium pyrophosphate | 2.5000 |
| Zinc carbonate $ZnCO_3$ | 1.0000 |
| Zinc lactate | 2.0000 |
| Example mixture 7 | 1.2000 |
| Total | 100.0000 |

Mouthwash

TABLE 43

Mouthwash

| Constituent | wt % |
| --- | --- |
| Deionized water | 79.5800 |
| 1,2-Propylene glycol | 2.0000 |
| Benzoic acid | 0.1200 |
| Cremophor CO 40 | 1.0000 |
| Ethyl alcohol, 96% | 5.0000 |
| Glycerol | 8.0000 |
| L-Blue 5000 (1% in water) | 0.1000 |
| Sodium sucrose 450 | 0.0500 |
| Sorbitol, 70% | 1.0000 |
| Hydrogen peroxide (35% $H_2O_2$ in water) | 3.0000 |
| Example mixture 6 | 0.1500 |
| Total | 100.0000 |

Mouthwash Concentrate

TABLE 44

Mouthwash concentrate

| Constituent | wt % |
| --- | --- |
| Deionized water | 49.6700 |
| Allantoin | 0.2000 |
| Colour L-Blue 5000 (1% in water) | 0.0300 |
| Cremophor CO 40 | 5.0000 |
| Ethyl alcohol, 96% | 42.0000 |
| Sodium sucrose 450 | 0.1000 |
| Example mixture 6 | 3.0000 |
| Total | 100.0000 |

Chewing Gum (Sugar-Containing and Sugar-Free)

TABLE 45

Chewing gums (sugar-containing and sugar-free)

| Constituent | A wt % | B wt % |
| --- | --- | --- |
| Confectioners' sugar | 61.7500 | — |
| Sorbitol (in powder form) | — | 38.6000 |
| Acesulfame K | — | 0.1000 |
| Aspartame | — | 0.1000 |
| Emulgum™ (emulsifier) | — | 0.3000 |
| Glucose syrup | 16.5000 | — |
| Glycerol | 0.5000 | 1.0000 |
| Gum base (chewing gum base) | 21.0000 | 30.0000 |
| Mannitol | — | 3.0000 |
| Palatinit | — | 9.5000 |
| Sorbitol, 70%, in water | — | 14.0000 |
| Xylitol | — | 2.0000 |
| Example mixture 7 | 0.2500 | 1.4000 |
| Total | 100.0000 | 100.0000 |

Candy

TABLE 46

Candy

| Constituent | wt % |
| --- | --- |
| Water | 2.7500 |
| Sugar | 60.1000 |
| Glucose syrup | 36.9000 |
| Example mixture 8 | 0.2500 |
| Total | 100.0000 |

Fine Fragrance

TABLE 47

Fine Fragrance 1

| Substance | wt % |
| --- | --- |
| 1,4-Cineole | 0.011 |
| 4-Hydroxyacetophenone | 5 |
| Ambrarome, 10% in IPM | 2 |
| Benzoin Siam resin, 50% in BB | 2.5 |
| Bouleau abs., 10% in IPM | 0.7 |
| Cedrene | 1.5 |
| *Cistus labdanum* abs., 10% in PG | 2.5 |
| Coumarin | 6 |
| Damascone beta, 10% in TRI | 1 |
| Dodecalactone-delta | 0.100 |
| Dodecalactone-gamma | 0.352 |
| DPG | 41.337 |
| Ethanol | 5.000 |
| Eugenol | 0.2 |
| Geraniol | 3.2 |
| Ionone beta | 1.5 |
| Iso E Super | 10 |
| Jasmol | 3 |
| Leather base (SUEDERAL LT) | 0.3 |
| Linalool | 1.5 |
| Linalyl acetate | 2 |
| Methyl cyclopentenolone-3,2,2, natural, 10% in DPG | 0.3 |
| Olibanum coeur, 50% in TEC | 3 |
| Oponax oil, 10% in DPG | 1 |
| Sandalore | 1 |
| Tolu resin, 50% in DPG | 1.5 |
| Vanillin | 2 |
| Vetiver oil java, 10% in DPG | 1.5 |
| Total | 100.0000 |

TABLE 48

Fine fragrance 2

| Substance | wt % |
| --- | --- |
| 4-HYDROXYACETOPHENONE | 0.6590 |
| AGRUNITRILE | 0.3405 |
| ALDEHYDE C12 MNA, 1% DPG | 0.4393 |
| ALCOHOL C10 | 0.0013 |
| ALLYL AMYL GLYCOLATE | 1.2630 |
| AMBERWOOD ® F | 0.2526 |
| AMBROCENIDE ®, 10 DPG | 0.2087 |
| AMBROXIDE, 10% IPM | 0.3295 |
| AMYL SALICYLATE | 1.5485 |
| BAY OIL | 0.0008 |
| BENZYL ACETATE | 1.1312 |
| BENZYL BENZOATE M | 0.0006 |
| BENZYL SALICYLATE | 5.7878 |
| BORNEOL L/ISOBORNEOL 65/35 | 0.0162 |
| BORNYL ACETATE L, CRYST. | 0.0005 |
| BUTYLENE CARBONATE | 0.2197 |
| CALONE, 10% DPG | 0.1428 |
| CAMPHENE L SUPRA | 0.1428 |
| CANTHOXAL | 0.1098 |
| CARDAMOM OIL | 0.0011 |
| CARYOPHYLLENE NAT. RECT. | 0.0079 |
| CASSIS ABS. BOURGEONS | 0.0003 |
| CEDAR LEAF OIL | 0.2636 |
| CEDAR WOOD OIL CHIN. | 0.0005 |
| CEDRAMBER | 2.8335 |
| CINNAMON LEAF OIL DISCOL. | 0.1647 |
| *CISTUS LABDANUM* ABS. SIS, 10% DPG | 0.1098 |
| CITRAL MELANGE | 0.0008 |
| CITRONELLOL 950 | 0.0280 |
| CITRONELLYL FORMATE | 0.0099 |
| CITRONELLYL TIGLINATE | 0.0049 |
| CITRIC ACID MONOHYDRATE MSF, 10% DPG | 0.9225 |
| COPAIBA BALSAM OIL ED | 0.0022 |
| COUMARONE | 0.1318 |
| COUMARIN | 0.4064 |
| CUMINALDEHYDE | 0.0549 |
| CUMINIC ALCOHOL | 0.0988 |
| CYMOL PARA SUPRA | 0.0003 |
| DAMASCONE DELTA | 0.0879 |
| DECALACTONE-GAMMA | 0.2197 |
| DEP | 0.5491 |
| DIHYDROEUGENOL | 0.0988 |
| DIHYDROMYRCENOL | 33.8484 |
| DIMETHYL SULFIDE/10% IN TEC | 0.0003 |
| DODECALACTONE-GAMMA | 0.4393 |
| DYNASCONE | 0.0001 |
| ETHANOL | 4.1930 |
| ETHYLHEXYLGLYCERIN | 0.1098 |
| EUCALYPTOL NAT. 80/85% | 0.0154 / 0.8913 |
| EUGENOL NAT. | 0.1192 |
| EVERNYL | 0.4173 |
| FARENAL ®, 10% DPG | 0.0988 |
| FENCHONE D, 10% DPG | 0.1098 |
| FLORAZONE | 0.0439 |
| FLORHYDRAL, 10% DPG | 0.0549 |
| FLOROSA BM/PYRANOL | 0.9775 |
| FRAMBINON ®, 10% DPG | 0.5821 |
| GALAXOLIDE PURE | 3.8439 |
| GALBANOLENE SUPER | 0.0879 |
| GERANIOL SUPRA | 0.0428 |
| GERANYL ACETATE 60 | 0.0028 |
| GERANYL FORMATE SUPRA | 0.0198 |
| GLOBALIDE ® | 0.5491 |
| GURJUN BALSAM OIL | 0.0071 |
| HEDIONE | 0.4064 |
| HELIOTROPIN/PIPERONAL | 0.2306 |
| HERCOLYN D-E | 0.0037 |
| HEXALACTONE GAMMA, 10% DPG | 0.2306 |
| HEXANEDIOL | 0.2197 |
| CIS,TRANS-3 | 0.0002 |
| HEXENOL CIS-3 | 0.1107 |
| HEXENYL ACETATE CIS,TRANS-3, 10% DPG | 0.1647 |
| HEXYL SALICYLATE | 2.0208 |
| HEXYL CINNAMALDEHYDE ALPHA | 4.3381 |
| ISO E SUPER | 14.1017 |
| ISOAMYL ALCOHOL | 0.0002 |
| ISOBORNYL ACETATE | 0.9225 |
| ISOBORNYL CYCLOHEXANOL | 1.4277 |
| ISOBUTYL QUINOLINE DL 100% | 0.0439 |
| ISOEUGENOL METHYL ETHER | 0.0004 |
| ISOMENTHONE | 0.0148 |
| CAMPHOR DL | 0.4064 |
| LAVANDIN OIL GROSSO NAT. CENSO | 0.0830 |
| LIGUSTRAL | 0.0010 |
| LIMONENE D PURE | 0.0785 |
| LINALOOL | 0.2166 |
| LINALOOL BM | 2.5260 |
| LINALOOL OXIDE | 0.0008 |
| LINALYL ACETATE | 0.1206 |
| MACIS OIL ND | 0.0879 |
| MAJANTOL ® | 0.3624 |
| MAJORAM OIL EGYPT. | 0.0004 |
| MALTOL | 0.0004 |
| MANDARIN ALDEHYDE, 10% IN TEC, 10% BB | 0.0879 |
| MANZANATE, 10% DPG | 0.2636 |
| MENTHANYL ACETATE | 1.1532 |
| MINTONAT | 0.4393 |
| MYRCENE | 0.0015 |
| NEROL 900 | 0.0016 |
| NEROLIDOL | 0.0033 |
| OCIMENE | 0.0022 |
| OCTANEDIOL | 0.2197 |
| OCTANONE-3 | 0.0012 |
| OCTENOL-1,3 | 0.0014 |
| ORANGE OIL, 5X | 0.0001 |
| *ORIGANUM* OIL | 0.0549 |
| OXANTHIA, 50% IN TEC | 0.0011 |
| PATCHOULI OIL DE. | 1.6254 |
| PELARGONIC ACID | 0.0002 |
| PENTANEDIOL | 0.2197 |
| PENTYL FORMATE | 0.0003 |
| PEPPER OIL BLACK, 10% BB | 0.2855 |
| *EUCALYPTUS* OIL | 0.0038 |
| PHENETHYL ALCOHOL | 0.0033 |
| PHENETHYL ALCOHOL | 0.1208 |
| *PIMENTA* OIL REF. A | 0.0002 |
| PINENE ALPHA LAEVO NAT. | 0.2855 |
| PINENE BETA NAT. | 0.0878 |
| PINOACETALDEHYDE | 0.0329 |
| PRECYCLEMONE B | 0.1318 |
| PROPANEDIOL | 0.8786 |
| RHUBOFIX | 0.0011 |
| ROSE OXIDE | 0.0016 |
| ROSE OXIDE HIGH CIS | 0.0001 |
| ROSEMARY OIL BM | 0.2636 |
| SANDRANOL ® | 0.6590 |
| STAR ANISE OIL CRUDE, 10% TEC | 0.0002 |
| TERPINENE GAMMA | 0.0002 |
| TERPINENOL-4 NAT. | 0.0020 |
| TERPINEOL ALPHA | 0.0030 |
| TERPINEOL PURE | 0.1195 |
| TERPINOLENE DEXTRO | 0.0003 |
| TETRAHYDROGERANIOL | 0.0000 |
| TONALIDE | 2.7457 |
| TRIETHYL CITRATE | 0.0584 |
| VELOUTONE | 0.0011 |
| VERTOCITRAL | 0.1647 |
| Total | 100.0000 |

Candy, Sugar-Free

TABLE 49

Candy

| Constituent | wt % |
| --- | --- |
| Isomalt | 95.0225 |
| Water | 2.2400 |

TABLE 49-continued

| Candy | |
|---|---|
| Constituent | wt % |
| Xylitol | 2.4000 |
| Sucralose | 0.0300 |
| Acesulfame K | 0.0500 |
| Citric acid | 0.0500 |
| Pellitorin solution (containing 10% pellitorin) | 0.0075 |
| Example mixture 8 | 0.2000 |
| Total | 100.0000 |

The invention claimed is:

1. A method of reduction and/or masking of undesired off-notes in oleochemical preparations, comprising adding a substance mixture comprising components (a), (b), and (c) wherein
(a) is at least one compound selected from the group consisting of
(a1) alcohol monoterpenes of formula (I)

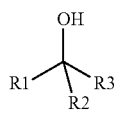

where R1 is H or methyl, R2 is H, and R3 is a linear or branched, saturated or unsaturated hydrocarbon radical having 4 to 10 carbon atoms, and also the enantiomers, diastereomers, racemates, solvates and physiologically compatible salts thereof,
(b) is at least two lactones of formula (II)

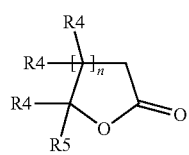

where R4 is H or methyl, R5 is a linear saturated hydrocarbon radical having 2 to 8 carbon atoms and n is the numbers 1 or 2, and also the enantiomers, diastereomers and racemates thereof, and
(c) is (c1) ethanol, and
(c2) at least one solvent selected from the group consisting of water, di-propylene glycol (DPG), diethyl phthalate (DEP), propylene glycol (PG), isopropyl myristate (IPM), isopropyl palmitate (IPP), triethyl cit-rate (TEC), triacetin (TRI), 1,2-propanediol, 1,3-propanediol, propanethiol, pentanediol, hexanediol, octanediol, decanediol, dodecanol, 4-hydroxyacetophenone, glycerol, butylene glycol, pentylene glycol, hexylene glycol, decylene glycol, propylene carbonate, butylene carbonate, glycerol carbonate, 2-benzylheptanol, laurylal-12-cohol, trimethyl hydroxypentyl isobutyrate, glyceryl caprylate, ethylhexylglycerin, benzyl benzoate (BB), and wherein the amounts of the components of the substance mixture are:
(i) 0.001% to 0.1% by weight of component (a)
(ii) 0.001% to 0.1% by weight of component (b)
(iii) 0.001% to 0.1% by weight of component (c)
with the proviso that the amount of ethanol is less than 10% by weight based on the weight of the substance mixture and amounts of (a), (b) and (c) and the substance mixture adds up to 100% by weight on the total weight of the substance mixture, and
wherein the undesired off-notes in the oleochemical preparations are caused by aldehydes of formula (III)

where R6 is a saturated or unsaturated, linear hydrocarbon radical, and/or free fatty acids of formula (IV)

where R7 is a linear or branched, saturated hydrocarbon radical.

2. The method of claim 1 comprising using the preparation as a fragrance or perfume.

3. The method of claim 1, component (a1) is selected from the group consisting of linalool, geraniol, freesiol and nerolidol.

4. The method of claim 1, wherein said substance mixture further comprises aroma substances or fragrances (component d) selected from the group consisting of 3-phenylbutanal, acetylmethylcarbinol, anethole, anisyl acetate, dihydroeugenol, linalyl formate, 2-methyldecanal, 2-benzyl-2-methylbut-3-enenitrile, 3-hexenyl acetate, styralyl acetate, citronellal, cinnamyl acetate, 2,4-dimethyl-4-phenyloxolane, beta-ionone, anther, prenyl acetate, 2-phenylpropanal, 4-(4-hydroxyphenyl)butan-2-one, ethyl phenoxyacetate, methyl ionone, gamma-terpinene, limonene, neocyclocitral, methyl lavender ketone, styralyl propionate, phenethyl propionate, limonenal, 4-isopentylcyclohexanol, 4-methyl-2-phenyl-3,6-dihydro-2H-pyran, 4-methylene-2-phenyltetrahydropyran, hydrocitronitrile, phenoxanol, isoamyl phenylacetate, damascone, 2-methyl-3-[4-(2-methylpropyl)phenyl]propanal, 2-[2-(4-methyl-3-cyclohexen-1-yl)propyl]cyclopentanone, (3aR,5aS,9aS,9 bR)-3a,6,6,9a-tetramethyl-2,4,5,5a,7,8,9,9b-octahydro-1H-benzo[e][1]benzofuran, acetyl pyrazine, trimethyl pyrazine, isoamyl acetate, para-cresyl methyl ether, filbertone, cyclohexyl acetate, heliotropin, acetophenone, anisaldehyde, para-methylacetophenone, veratraldehyde, and methyl anisate.

* * * * *